(12) United States Patent
Alzamzmi et al.

(10) Patent No.: US 10,827,973 B1
(45) Date of Patent: Nov. 10, 2020

(54) MACHINE-BASED INFANTS PAIN ASSESSMENT TOOL

(71) Applicant: University of South Florida, Tampa, FL (US)

(72) Inventors: Ghadh A. Alzamzmi, Tampa, FL (US); Dmitry Goldgof, Lutz, FL (US); Yu Sun, Tampa, FL (US); Rangachar Kasturi, Tampa, FL (US); Terri Ashmeade, Tampa, FL (US)

(73) Assignee: University of South Florida, Tampa, FL (US)

( * ) Notice: Subject to any disclaimer, the term of this patent is extended or adjusted under 35 U.S.C. 154(b) by 1298 days.

(21) Appl. No.: 14/989,500

(22) Filed: Jan. 6, 2016

Related U.S. Application Data

(60) Provisional application No. 62/186,956, filed on Jun. 30, 2015.

(51) Int. Cl.
*A61B 5/00* (2006.01)
*A61B 5/0205* (2006.01)

(52) U.S. Cl.
CPC .......... *A61B 5/4824* (2013.01); *A61B 5/0077* (2013.01); *A61B 5/0205* (2013.01); *A61B 5/4803* (2013.01); *A61B 5/4836* (2013.01); *A61B 5/7267* (2013.01); *A61B 2503/04* (2013.01); *A61B 2562/0204* (2013.01); *A61B 2562/0266* (2013.01)

(58) Field of Classification Search
CPC ...... A61B 5/4824; A61B 5/0013; A61B 5/746
See application file for complete search history.

(56) References Cited

U.S. PATENT DOCUMENTS

| | | | |
|---|---|---|---|
| 8,764,650 | B2 | 7/2014 | Schiavenato et al. |
| 2006/0128263 | A1 | 6/2006 | Baird |

(Continued)

FOREIGN PATENT DOCUMENTS

| | | |
|---|---|---|
| CN | 107491740 A | 12/2017 |
| WO | 2014036263 A1 | 3/2014 |

OTHER PUBLICATIONS

Holsti, Liisa, et al. "Body movements: an important additional factor in discriminating pain from stress in preterm infants." The Clinical journal of pain 21.6 (2005): 491. (Year: 2005).*

(Continued)

*Primary Examiner* — Vincent Rudolph
*Assistant Examiner* — Raphael Schwartz
(74) *Attorney, Agent, or Firm* — Smith & Hopen, P.A.; Molly L. Sauter

(57) ABSTRACT

A system and method for measuring an infant's pain intensity is presented. The method for assessing an infant's pain intensity based on facial expressions is comprised of three main stages: detection of an infant's face in video sequence followed by preprocessing operations including face alignment; expression segmentation; and expression recognition or classification. Also presented is a multimodal system for assessing an infant's pain intensity using the following classifiers: facial expression classifier; vital sign classifier; crying recognition classifier; body motion classifier and state of arousal classifier. Each classifier generates an individual score, all of which are normalized and weighed to generate a total pain score that indicates pain intensity.

24 Claims, 13 Drawing Sheets

(56) References Cited

U.S. PATENT DOCUMENTS

| | | | |
|---|---|---|---|
| 2008/0235030 A1* | 9/2008 | Sisto | G10L 17/26 |
| | | | 704/275 |
| 2012/0088985 A1* | 4/2012 | Schiavenato | A61B 5/4824 |
| | | | 600/301 |
| 2014/0276188 A1 | 9/2014 | Jardin | |

OTHER PUBLICATIONS

Shreve, Matthew, et al. "Macro-and micro-expression spotting in long videos using spatio-temporal strain." Face and Gesture 2011. IEEE, 2011. (Year: 2011).*

Lu, Guanming, Xiaonan Li, and Haibo Li. "Facial expression recognition for neonatal pain assessment." 2008 International Conference on Neural Networks and Signal Processing. IEEE, 2008. (Year: 2008).*

Hazelhoff, Lykele, Jungong Han, and Sidarto Bambang-Oetomo. "Behavioral state detection of newborns based on facial expression analysis." International Conference on Advanced Concepts for Intelligent Vision Systems. Springer, Berlin, Heidelberg, 2009. (Year: 2009).*

Arif-Rahu et al., "Bio behavioral measures for pain in the pediatric patient." Pain Management Nursing 13.3 (2012): pp. 157-168.

Bagnato et al. "Robust infants face tracking using active appearance models: a mixed-state Condensation approach." Advances in Visual Computing. Springer Berlin Heidelberg, 2007. pp. 13-23.

Beauchemin et al., "The computation of optical flow." ACM Computing Surveys (CSUR) vol. 27, No. 3 (1995): pp. 433-466.

Brahnam et al., "Introduction to neonatal facial pain detection using common and advanced face classification techniques." Advanced Computational Intelligence Paradigms in Healthcare-1. Springer Berlin Heidelberg, 2007. pp. 225-253.

Brahnam, et al., "Machine assessment of neonatal facial expressions of acute pain." Decision Support Systems vol. 43, No. 4 (2007): pp. 1242-1254.

Brahnam et al., "Machine recognition and representation of neonatal facial displays of acute pain." Artificial intelligence in medicine vol. 36, No. 3 (2006): pp. 211-222.

Craig, K.D., et al., Pain in the preterm neonate: behavioural and physiological indices. Pain, 1993. vol. 52, No. (3): pp. 287-299.

Fournier-Charriere et al., "EVENDOL, a new behavioral pain scale for children ages 0 to 7years in the emergency department: Design and validation." PAIN® vol. 153, No. 8 (2012): pp. 1573-1582.

Gholami et al., "Agitation and pain assessment using digital imaging." Engineering in Medicine and Biology Society, 2009. Embc 2009. Annual International Conference of the IEEE, 2009, pp. 1-13.

Hall et al., "The WEKA data mining software: an update." ACM SIGKDD explorations newsletter vol. 11, No. 1, (2009): pp. 1-10.

Hammal et al., "Automatic detection of pain intensity." Proceedings of the 14th ACM international conference on Multimodal interaction. ACM, 2012, pp. 1-6.

Hicks et al., "The Faces Pain Scale—Revised: toward a common metric in pediatric pain measurement." Pain vol. 93, No. 2 (2001): pp. 173-183.

Holsti et al., Specific Newborn Individualized Developmental Care and Assessment Program movements are associated with acute pain in preterm infants in the neonatal intensive care unit. Pediatrics, 2004. vol. 114, No. 1: pp. 65-72.

Hummel, P.A., et al., Clinical reliability and validity of the N-PASS: neonatal pain, agitation and sedation scale with prolonged pain. Journal of perinatology, 2003. vol. 28, No. 1, pp. 55-60.

Johnston et al., "Experience in a neonatal intensive care unit affects pain response." Pediatrics vol. 98, No. 5 (1996): pp. 925-930.

Kohavi, "A study of cross-validation and bootstrap for accuracy estimation and model selection." IJCAI, vol. 14. No. 2. 1995, pp. 1-8.

Lienhart et al., An Extended Set of Haar-like Features for Rapid Object Detection. IEEE ICIP 2002, vol. 1, pp. 900-903, Sep. 2002.

Lindh et al. "Heel lancing in term new-born infants: an evaluation of pain by frequency domain analysis of heart rate variability." Pain vol. 80, No. 1 (1999): pp. 143-148.

Nanni et al., "A local approach based on a Local Binary Patterns variant texture descriptor for classifying pain states." Expert Systems with Applications vol. 37, No. 12 (2010): pp. 7888-7894.

Saragih et al., "Face alignment through subspace constrained mean-shifts". In International Conference of Computer Vision, Sep. 2009, pp. 1-8.

Shreve et al., "Automatic Expression Spotting in Videos", Image and Vision Computing, vol. 32, No. 8, pp. 476-486, 2014.

Shreve et al., "Macro- and micro- expression spotting in long videos using spatio-temporal strain". International Conference on Automatic Face and Gesture Recognition, pp. 51-56, c 2012 IEEE, Mar. 2011.

Shreve et al., "Towards macro- and micro- expressions spotting in videos using strain patterns". Workshop on Applications of Computer Vision, Dec. 2009, pp. 1-6.

Valeri et al., Pain in preterm infants: Effects of sex, gestational age, and neonatal illness severity. Psychology & Neuroscience. vol. 5, No. 1, pp. 11-19.

Viola et al., Rapid Object Detection using a Boosted Cascade of Simple Features. IEEE CVPR, 2001, pp. I-511-I-518.

Viola et al., "Robust real-time face detection." International journal of computer vision vol. 57, No. 2, (2004): pp. 137-154.

Wilson et al., "Facial feature detection using Haar classifiers." Journal of Computing Sciences in Colleges vol. 21, No. 4 (2006): pp. 127-133.

Evans et al., Longitudinal comparison of preterm pain responses to repeated heelsticks. Pediatric nursing, 2005. vol. 31, No. 3: pp. 216-221.

Fotiadou et al., "Video-based facial discomfort analysis for infants", Proc. SPIE 9029, Visual Information Processing and Communication V, 90290F, 2014, pp. 1-14.

Gibbins, S., et al., Comparison of pain responses in infants of different gestational ages. Neonatology, 2008. vol. 93, No. 1: pp. 10-18.

Hudson-Barr et al., Validation of the pain assessment in neonates (PAIN) scale with the neonatal infant pain scale (NIPS). Neonatal Network. vol. 21, No. 6: pp. 15-21.

Petroni, Marco, et al. "Identification of pain from infant cry vocalizations using artificial neural networks (ANNs)." SPIE's 1995 Symposium on OE/Aerospace Sensing and Dual Use Photonics. International Society for Optics and Photonics, vol. 2492, pp. 729-737.

Brahnam et al., "Neonatal Facial Pain Detection Using NNSOA and LSVM." Ipcv. 2008, pp. 1-7.

Anand, "Consensus statement for the prevention and management of pain in the newborn." Archives of pediatrics & adolescent medicine vol. 155, No. 2, (2001): pp. 173-180.

Allegaert et al., Variability in pain expression characteristics in former preterm infants, J. Perinat. Med. vol. 33, No. 5, (2005) pp. 442-448.

Hummel et al., N-PASS: Neonatal Pain, Agitation and Sedation Scale—Reliability and Validity, Poster presented at: the Pediatric Academic Societies annual meeting, Pediatrics/Neonatology, Loyola University Medical Center, Maywood, IL Perinatal Center, Oncology Institute, vol. 2, N. 6, Nov. 2004, pp. 1-4.

Lawrence, "The development of a tool to assess neonatal pain." Neonatal network: NN vol. 12, No. 6, (1993): pp. 59-66.

* cited by examiner

FIG. 1A
FIG. 1B
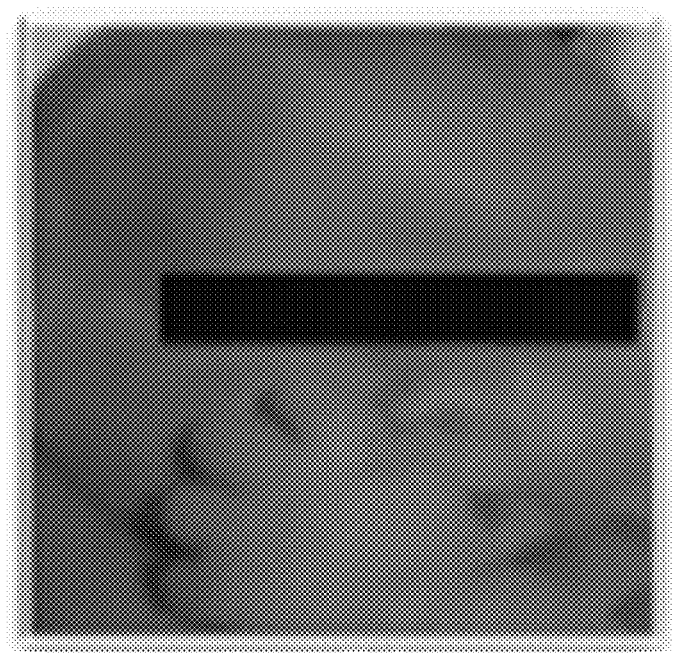

FIG. 1C
FIG. 1D

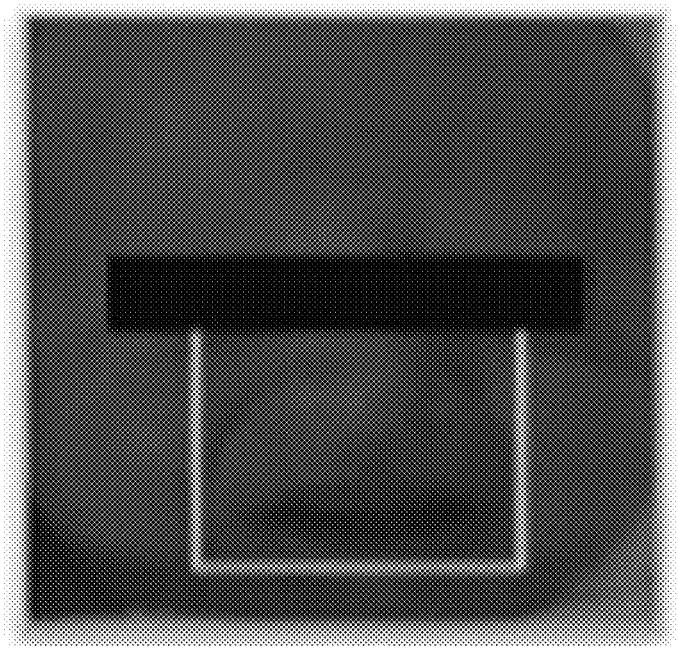
*FIG. 2A*
*FIG. 2B*

Mathematical Formulation of the Isolated Acute Pain Model

*FIG. 12A*

Let:
$X_1$ = facial expression, (0-1)
$X_2$ = vital signs, (0-1)
$X_3$ = crying, (0-1-2)
$X_4$ = body motions, (0-1)
$X_5$ = state of arousal, (0-1)

Then, the multivariable regression model can be defined as:
$$Y_p = b_1 X_1 + b_2 X_2 + b_3 X_3 + b_4 X_4 + b_5 X_5 + b_0$$

Where: $Y_p$ = response variable (i.e., total pain score (0-7))
$X_{1-5}$ = predictor variables (i.e., features vectors)
$b_{1-5}$ = the features' coefficients or weights, and
$b_0$ = error.

*The values of these weights can vary based on the infant's group*

Pain Threshold (PT) = $\begin{cases} \text{If } Y_p = 0\text{-}2, \text{ No pain} \\ \text{If } Y_p = 3\text{-}4, \text{ Moderate pain} \\ \text{If } Y_p >= 4, \text{ Severe pain} \end{cases}$

Mathematical Formulation of the Prolonged Acute Pain Model

*FIG. 12B*

Let:
$X_1$ = facial expression, (0-2)
$X_2$ = vital signs, (0-2)
$X_3$ = crying, (0-2)
$X_4$ = body motion, (0-2)
$X_5$ = state of arousal, (0-2)

Then, the multivariable regression model is defined as:
$$Y_p = b_1 X_1 + b_2 X_2 + b_3 X_3 + b_4 X_4 + b_5 X_5 + b_0$$

Where: $Y_p$ = response variable (i.e., total pain score (0-10))
$X_{1-5}$ = predictor variables (i.e., features vectors)
$b_{1-5}$ = the features' coefficients or weights, and $b_0$ = error.

*The values of these weights can vary based on the infant's group*

Group 1:
PT = $\begin{cases} \text{If } Y_p >= 6, \text{ Pain} \\ \text{Otherwise, No pain} \end{cases}$ Group 2:
PT = $\begin{cases} \text{If } Y_p >= 5, \text{ Pain} \\ \text{Otherwise, No pain} \end{cases}$ Group 3:
PT = $\begin{cases} \text{If } Y_p >= 4, \text{ Pain} \\ \text{Otherwise, No pain} \end{cases}$ Group 4:
PT = $\begin{cases} \text{If } Y_p >= 3, \text{ Pain} \\ \text{Otherwise, No pain} \end{cases}$

MACHINE-BASED INFANTS PAIN ASSESSMENT TOOL

CROSS-REFERENCE TO RELATED APPLICATIONS

This nonprovisional application is a continuation of and claims priority to U.S. Provisional Patent Application No. 62/186,956, entitled "Machine-Based Infants Pain Assessment Tool", filed Jun. 30, 2015 by the same inventors, the entirety of which is incorporated herein by reference.

FIELD OF INVENTION

This invention elates, generally, to a system and method for use in assessing pain. More specifically, the invention relates to a system and method of assessing pain in an infant based on a series of behavioral and physiological pain indicators.

BACKGROUND OF THE INVENTION

Pain is an important indicator that is used by health professionals to understand the patient's medical condition and develop suitable treatment plans. To diagnose pain, health professionals usually depend on the patient's verbal or nonverbal self-reporting in the case of children. Faces Pain Scale (ITS) [1] is one of the most popular non-verbal self-reporting methods. FPS employs a set of drawn faces with different expressions (e.g., discomfort, pain) to measure a child's pain intensity. This scale is useless, however, in the case of infants.

Infants' pain assessment is challenging since infants do not have the ability to communicate or articulate their pain experience. Assessing their pain depends primarily on the subjective judgments of nurses who monitor infants periodically and observe signs of pain [2]. Therefore, it is important to build an objective pain assessment system to measure infants' pain intensity based on physiological (e.g., vital signs, changes in skin color, and pupil dilation) and/or behavioral (e.g., pain expression, crying, and body movements) pain indicators. An advantage of the machine-based pain assessment is that it can provide a consistent and minimally biased pain assessment tool that is capable of reducing the subjectivity and burden/cost of continuous monitoring.

Automated infant pain assessment systems are a recent topic in computer vision. Several researchers have studied the machine assessment of infant pain based on various indicators. Petroni et al. introduced the first application for infant cry classification [3]. They classified and discriminated the infant cry of pain from other cries (e.g., hunger or discomfort) by extracting the mel-cepstrum coefficients from voice signals as features and feeding them to a neural networks classifier.

Lindh et al. introduced a study [4] to assess the pain based on heart rate variability (HRV) during heel lancing procedure. The results of this study have shown that there is a strong relation between pain intensity and an increase in the heart rate (i.e., the heel squeezing, which is considered the most painful event during heel lancing procedure, generates the highest heart beat rate).

Brahnam et al. proposed the first work [5], which is known as the COPE (Classification of Pain Expressions) project, to detect pain expression based on analysis of infants' facial displays. Three face classification techniques principal component analysis (PCA), linear discriminant analysis (LDA), and support vector machine (SVM) were applied to distinguish facial expression of pain from other expressions. These classifiers were applied on the COPE dataset, which consisted of 204 color images of 26 infants taken under four pain stimuli. The best recognition rate of pain expression versus no-pain expressions was 88% with the SVM classifier. Other studies, which used the same dataset to detect pain in infants' face, can be found in [6-10].

U.S. Pat. No. 8,764,650 to Schiavenato et al. discloses a method of communicating a pain level of a patient during a clinical procedure using skin/flexure input sensors using Boolean logic or neural network to process the input data. A pain score is generated during the procedure, and a future pain score is generated as well. The sensors used in the '650 patent are not capable of analyzing voice data and further are subject to incorrect placement due to infant movement which would then provide incorrect measurements. In addition, the '650 patent measures facial grimacing using a flexure input sensor around the mouth. It is difficult to distinguish between expressions based on mouth motions using this technique of measurement because mouth motion can correspond to several other expressions besides pain, such as sadness, discomfort, sucking on a pacifier, etc. As will become clearer as this specification continues, voice can be one of the most important pain indicators for infants. Analyzing voice can be particularly important with infants who cannot make the pain expression as a result of facial tissues deformations.

Hammal et al. disclose a method of facial pain recognition using the Active Appearance Model (AAM) algorithm. Hammal et al. measured adult pain intensity based on analysis of their facial expressions. As discussed herein, monitoring adult expressions is quite different than monitoring infant's expressions. Hammal uses action units (AU), requiring labeling of each action frame, and further, the classifier has to learn each action unit individually and does not work under occlusion.

The paper by Fotiadou et al., entitled "Video-based facial discomfort analysis for infants", discusses the use of video and the AAM to track the global motion and inner features of an infant's face to assess pain. The system detects discomfort by employing the AAM representations of the face on a frame-by-frame basis, using a Support Vector Machine (SVM) classifier. The AAM algorithm requires significant pre-training and classification and is very computationally intensive since it uses facial landmarks, shape, and skin texture. The AAM requires re-training and classification for different populations (e.g. different groups with different facial features) if the initial set is not very large and diverse. The AAM requires labeling the facial landmarks in each frame, and then these landmarks are used to build the model. AAMs are generally defined by a shape component and an appearance component, which jointly represent the shape and texture variability of the face. These components are generally fitted through a gradient-descent search. However, Fotiadou is overly labor- and computationally-intensive, and uses only one input (facial expression) to make its determination, which may be inaccurate or incomplete.

A paper on Evendol by Fournier-Charriere et al. (hereinafter "Evendol") discloses a paper-based 5-item scale for measuring pain in young children in emergency rooms. In use, the following 5 items are scored: vocal or verbal expression; facial expression; movements; postures; and interaction with environment. The scoring system ranges from 0 to 3 with 0=absent; 1=weak or transient; 2=moderate or present about half the time; and 3=strong or present almost all of the time. The items are scored at 4 different time intervals: upon arrival; before any painful stimulus; during examination of the painful area; and after administration of any analgesic treatment. Nurses score the child's pain manually on paper. This manual scoring can be highly subjective and thus subject to error and demands significant effort in monitoring infants and observing pain's signs.

U.S. Patent Application Publication No. 2006/0128263 to Baird discloses a computerized method for assessing opinions and feelings of a patient by changing the facial expression of a static image over time based on user input. The method of Baird depends on the patient being able to communicate their feelings, i.e. the patient in Baird chooses the face that describes their current feeling and as such is not applicable to assessing an infant's pain. This communication is not possible for infants since they cannot provide a user input; and as such, Baird would be unable to assess pain in such a patient.

International Patent Application Publication No. WO 2014/036263 to Sheinkopf et al. discloses a computerized method and apparatus for analyzing an infant's cry to assess an infant's pain and health condition. Sheinkopf only assesses an infant's crying, which would result in an incomplete and inaccurate pain assessment (Sheinkopf presents only a single model).

U.S. Patent Application Publication No. 2014/0276188 to Jardin discusses a method of assessing the pain level of a patient by using an algorithm to correlate EEG data with the patient's self-assessment level of the pain. Jardin would not be applicable to infant's pain since an infant is unable to provide a self-assessment of their pain level.

A paper by Arif-Rahu et al. entitled "Biobehavioral Measures for Pain in the Pediatric Patient" discusses the importance of using various pain indictors in assessing pain. Existing works focus on classifying infants' static images as pain or no-pain using existing algorithms, such as LBP, PCA, and SVM. However, video sequences and facial expressions of pain are not used, which may provide a more accurate assessment of pain. As will become clearer as this specification continues, assessing pain expression over time (i.e., video sequences) can be important to provide an accurate pain assessment since the pain changes and evolve over time, and a video-based pain assessment can be important to build a real-time application for clinical use.

Accordingly, what is needed is a consistent and minimally biased machine-based pain assessment tool to monitor infants and measure their pain intensity based on behavioral (e.g., pain expression, crying, and body movements) and physiological (e.g., vital signs) pain indicators. However, in view of the art considered as a whole at the time the present invention was made, it was not obvious to those of ordinary skill in the field of this invention how the shortcomings of the prior art could be overcome.

All referenced publications are incorporated herein by reference in their entireties. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

SUMMARY OF INVENTION

The long-standing but heretofore unfulfilled need for a comprehensive, accurate, and minimally biased and consistent pain assessment tool for individuals who are incapable of clearly communicating said pain is now met by a new, useful, and nonobvious invention.

In an embodiment, the current invention is a system for measuring or evaluating pain intensity experienced by a subject that is incapable clearly orally communicating the pain or that is capable of communicating the pain through only a behavioral indicator (e.g., an infant, an individual with dementia, etc.). The system includes a data reading device (e.g., A/V recorder such as a camera and/or microphone, vital signs reader) for visualizing and recording the subject's facial expressions, infant's voice, vital signs readings, and body movement including arms/legs. A facial expression classifier is used for evaluating the pain via the subject's facial expressions, where the facial expression classifier produces a facial expression score based on the subject's facial expressions. A voice classifier is used for evaluating the pain via the inarticulate sounds made by the subject (e.g., an infant's crying), where the voice classifier produces a voice score based on the frequency and pitch of those inarticulate sounds (e.g., using speech signal analysis). A vital signs classifier is used for evaluating the pain via the subject's physical condition (e.g., heart rate, breathing rate, oxygen saturation, changes in cerebral deoxyhemoglobin concentration, etc.), where the vital signs classifier produces a vital signs score based on the subject's physical condition. The system further includes a processor that runs a machine learning algorithm (e.g., parametric, non-parametric, optical flow, facial strain, local binary patterns, linear predictive coding, linear regression, neural network) for processing images, videos, signals, and/or a combination thereof. The facial expression score, voice classifier score, body motions score, and vital signs score are combined/weighed to produce a total score for pain assessment. The system also includes an output device for outputting the total score for pain assessment. Optionally, if the total score exceeds a predetermined threshold, a therapy or intervention can automatically be indicated by the output device as well.

Optionally, a body movement classifier may be used for evaluating the pain via the subject's motions that may correspond to the pain, where the body movement classifier produces a body movement score based on these motions. In this case, the body movement score would be combined with the other scores as well for the total score. These motions could indicate the subject's behavior state, arousal state, and extremities tone.

The facial expression classifier may evaluate pain intensity based on the subject's facial strain. Further, the facial strain can be trained using k Nearest-Neighbor and support vector machine for pain or no-pain experienced by the subject. Alternatively or in addition, detection of the facial strain can be accomplished via a modified strain algorithm predicated on movement of the subject's face.

The facial expression classifier may segment the subject's face into regions in order to provide the facial expression score even when a segment of the subject's face is obstructed or occluded. This permits partial facial detection.

Alternatively or in addition, the facial expression classifier may include (1) facial detection where the subject's face is detected, (2) expression segmentation where the subject's face is segmented into regions, and (3) expression recognition where pain can be detected. The facial detection may be achieved by detecting landmarks on the subject's face. For example, a landmark can be the subject's nose, in which case a digital mask is expanded around the nose to also include the eyes and surrounding area of the face. The facial detection function may train the facial expression classifier with positive images including these landmarks and negative images that do not include the landmarks. Alternatively or in addition, the facial detection function may train the facial expression classifier using an adaptive boosting algorithm.

During expression segmentation, there may be four (4) regions, wherein an optical flow vector generated for each region for the subject's face, such that the optical flow vector is used to estimate optical strains, which are then summed to generate an overall strain magnitude. This overall strain magnitude is related to the facial expressions that can indicate pain experienced by the subject.

Expression recognition may be achieved by applying a peak detector to detect points of maximum strain, wherein the maximum strain is related to the facial expressions that can indicate the subject's pain.

Regarding the voice classifier, frequency-based features may be extracted from the inarticulate sounds to represent audio segments that are used to train the voice classifier.

In a separate embodiment, the current invention may include any one or more or even all—of the foregoing features and characteristics of the system.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which:

FIGS. 1A-1D are a series of images depicting examples of challenges of tracking and detecting facial expression in a real-time clinical setting. FIG. 1A depicts strong head movement; FIG. 1B depicts self-occlusion; and FIGS. 1C-1D depict occlusion by external items such as a toy and a pacifier. Eyes are masked to protect privacy.

FIGS. 2A-B are a series of images depicting that the nose is detected first and then the mask is expanded to include the eyes and surrounding areas. This image depicts the manual face tracking that was used at the beginning of the study. An automated algorithm is now used to detect the face.

FIGS. 12A-12B depict the models' mathematical formulations, according to certain embodiments of the current invention.

DETAILED DESCRIPTION OF THE PREFERRED EMBODIMENT

Figure 3:
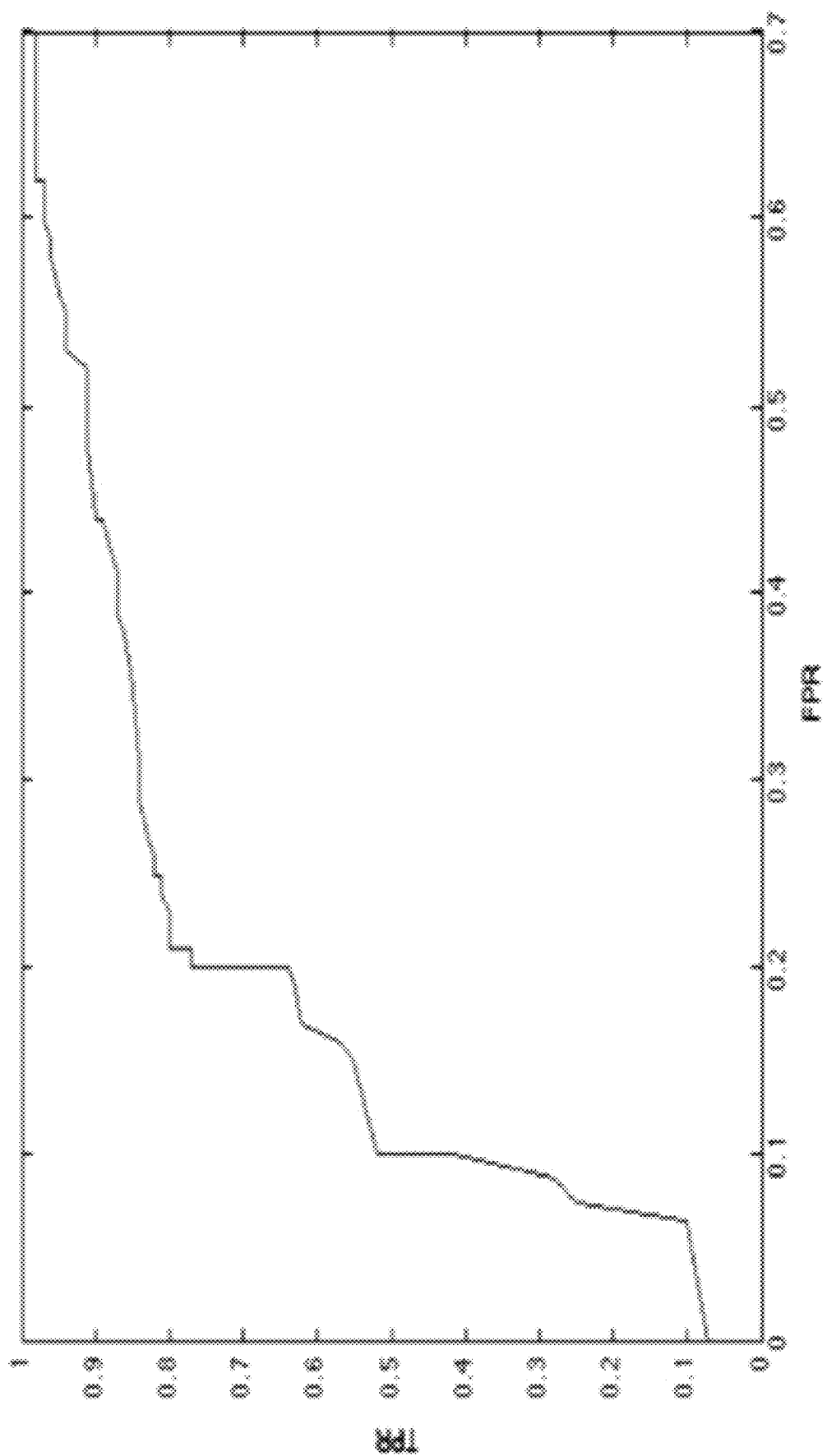
FIG. 3 is a graphical illustration depicting ROC curve of expression-spotting algorithm for 10 subjects. ROC achieves 80% TPR with 19% FPR.

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

As used in this specification and the appended claims, the singular forms "a", "an", and "the" include plural referents unless the content clearly dictates otherwise. As used in this specification and the appended claims, the term "or" is generally employed in its sense including "and/or" unless the context clearly dictates otherwise.

In an embodiment, the current invention is a method and system for assessing pain in an infant or other subject/individual who is incapable of clearly orally communicating pain levels/intensity. Specifically, a method and associated algorithm were developed for using an infant's facial expressions to determine a pain score using a modified strain algorithm. Unexpected results were obtained utilizing infant facial tissue distortion as a pain indicator in video-sequences of ten (10) infants based on analysis of facial strain. Facial strain, which is used as the main feature for classification, is generated for each facial expression and then used to train two classifiers, k Nearest-Neighbors (KNN) and support vector machine (SVM), to classify infants' expressions into two categories, pain and no-pain. The accuracy of binary classification for KNN and SVM was 96% and 94%, respectively, based on the ten (10) video sequences.

In an embodiment, the current invention is a machine-based infant pain assessment tool and methodology developed based on a series of behavioral and physiological pain indicators. This tool monitors infants continuously, detects various pain indicators (e.g., facial expression of pain, crying, body motion and changes in heart rate), and generates a total pain score based on these indicators.

In practice, this tool may be used in neonatal intensive care unit (NICU) to reduce clinical assessment subjectivity and reduce the costs of continuous monitoring of infants. It also can be used as a home-monitoring tool or in developing countries, where there is a lack of medical workers/supplies.

The novel system monitors infants at all times (not just during a certain procedure or period) using an audio/video recorder, as opposed to the input sensors seen in the prior art. Specifically, the audio/video recorder is used to visualize and record facial expressions, voice, state of arousal, and body movement including arms/legs. The use of the audio/video recorder as opposed to input sensors (e.g., flexure input sensors) is important because pain expression should be recognized by considering other parts of the face, not just the mouth. It is an object of the present invention to assess infants' pain on video sequences by utilizing multiple inputs, for example infants' facial expression of pain. It presents unexpected results for infants' pain assessment based on analysis of facial strain [11-13]. The present invention is the first to address assessing infants' pain dynamically for monitoring purposes based on this type of analysis.

Certain embodiments of the current invention also utilize image/video/signal processing and machine learning techniques to generate an executable code to measure an infant's pain intensity continuously. This technique, when used, is known in the art to be very different from using Boolean logic or neural network to process the input data. The data from the instant invention is capable of generating a total score that can be sent wirelessly to a remote station or be displayed digitally or visually on the infant's incubator. The system can be used both in clinical settings and in non-clinical settings, as skin electrodes and other medical devices are not typically utilized.

In certain embodiments, the system includes an algorithm generally based on the strain algorithm, which is predicated on motion, requires no pre-training and segments the face into regions, allowing for partial facial recognition. Partial facial recognition is important because infants are frequently moving and often have one or more parts of their faces obstructed. In addition, the pain assessment system of the instant invention uses multiple inputs for infant pain such as vital signs, body movement, and voice (e.g., cry), as well as facial expression, to generate a total pain score.

It should be noted that the instant invention is directed towards individuals who cannot communicate their pain in any way other than a behavioral indicator, such as facial expression, body motion, crying, etc. Examples of such an individual include, but are not limited to, infants, individuals who are mute, individuals with communicative/neurologic impairments (e.g., dementia), etc.

Study—Development of Infant Facial Expression Recognition Model

Novel, unexpected results of utilizing facial expression as a behavioral indicator of pain were found herein. The method has three main stages—face detection, expression segmentation, and expression recognition. Manual detection of an infant's face was performed at the beginning to extract facial points and were used for cropping and registration. A strain algorithm was employed to segment expressions by exploiting the non-rigid facial motion that occurs during facial expressions [11-13]. The accuracy of classifying the segmented expressions as pain or no-pain using KNN and SVM was 96% and 94%, respectively. Pain was assessed dynamically using infants' facial expression based on facial strain analysis.

A. Dataset

A challenging set of infants' video sequences was collected for the purpose of building a real-time pain assessment system. The procedure for collecting the data complied with the protocols and ethical directives for research involving human subjects at the University of South Florida. Prior to data collection, informed consent was obtained from the infants' parents.

Video sequences for a total of 10 subjects older than 30 weeks gestational age (e.g., premature and infants) were recorded under two different pain conditions: acute and chronic. The video sequences of nine (9) subjects were recorded during the acute pain procedure, and the remaining one (1) was recorded during the chronic pain procedure.

B. Procedure

As noted, the video sequences were recorded during two pain procedures: the acute and chronic pain procedures. Acute pain recordings were carried out during heel lancing procedures that were previously scheduled for routine blood test. Nine (9) subjects were recorded during the acute pain procedure in the presence of nurses who filled the score sheets using NIPS (Neonatal Infant Pain Scale) scoring tool. The scores were taken prior to, during, and after the procedure. These scores were used as ground-truth, which were compared later to the results of the method.

The infant with chronic pain was monitored during the post-operative recovery for approximately two (2) hours in the presence of nurses who scored the pain using an NPASS (Neonatal Pain, Agitation, and Sedation Scale) scoring tool at different intervals [14-16].

Table I summarizes the recording procedure for acute and chronic pain.

TABLE I

Summary of acute and chronic pain procedures.

| | Acute Pain | Chronic Pain |
|---|---|---|
| Pain Trigger | Imunization and heel lancing | Postoperative: G tube[1] |
| Pain Scale | NIPS | NPASS |
| Procedure | Acquire the infant's behavioral/physiological data before the pain procedure, at the start of the pain procedure, and after the completion of the procedure. NIPS pain scores were taken prior to, during, and after the acute procedure | Acquire the infant's behavioral/physiological data at the normal state before the operation and during post-operative periods for approx. 2 hours. NPASS pain scores were taken during the post-operative period every 15 minutes. |

[1] a tube is inserted into the infant stomach for the purpose of feeding her/him.

i. Methodology

In an embodiment, the instant pain expression recognition method includes three stages:
- A. Detection of an infant's face in video sequence followed by preprocessing operations including face alignment.
- B. Expression segmentation.
- C. Expression recognition or classification.
- C. Face Tracking and Registration The first stage in developing a pain recognition system is detecting and tracking an infant's face in a video sequence. There are several known face detection algorithms that can detect and track faces with high accuracy. Most of these algorithms perform well in detecting adult faces, but fail in cases of infants due to several reasons [17], including the fact that existing algorithms are developed and trained based on adult faces, which have different features than infants' faces. Further, detecting infants' faces is a challenging problem because infants make unpredictable movements (i.e., infants make different and strong out-of-plane head movements) and occlude their face (i.e., self-occlusion by hand or occlusion by external items such as a pacifier). As such, these conventional face detection mechanisms have significant difficulties detecting and tracking infants' faces.

FIGS. 1A-1D show examples of these challenges. In the current study, the results of applying several face tracking implementations on the infants' video sequences were not satisfactory. For instance, the results of running the mean shift face tracker [18], which is a robust face tracker to automatically detect and track 66 points on the face were insufficient. The results of running the MATLAB's implementation of Viola-Jones [19] were also insufficient.

Due to these results and the difficulties of using conventional face detection software with infants, the landmark points of the infants' face were manually extracted by first detecting their nose (see FIG. 2A) using the MATLAB's implementation of a cascade object detector. Even though the nose detector was trained for adults, the detector was able to accurately detect infants' nose. The mask around the nose was then expanded to include eyes and the surrounding area, as seen in FIG. 2B. After faces are located, face alignment was performed by transferring each face image in a video sequence to match the original starting location of the face.

D. Expression Segmentation Based on Facial Strain

Figure 5:
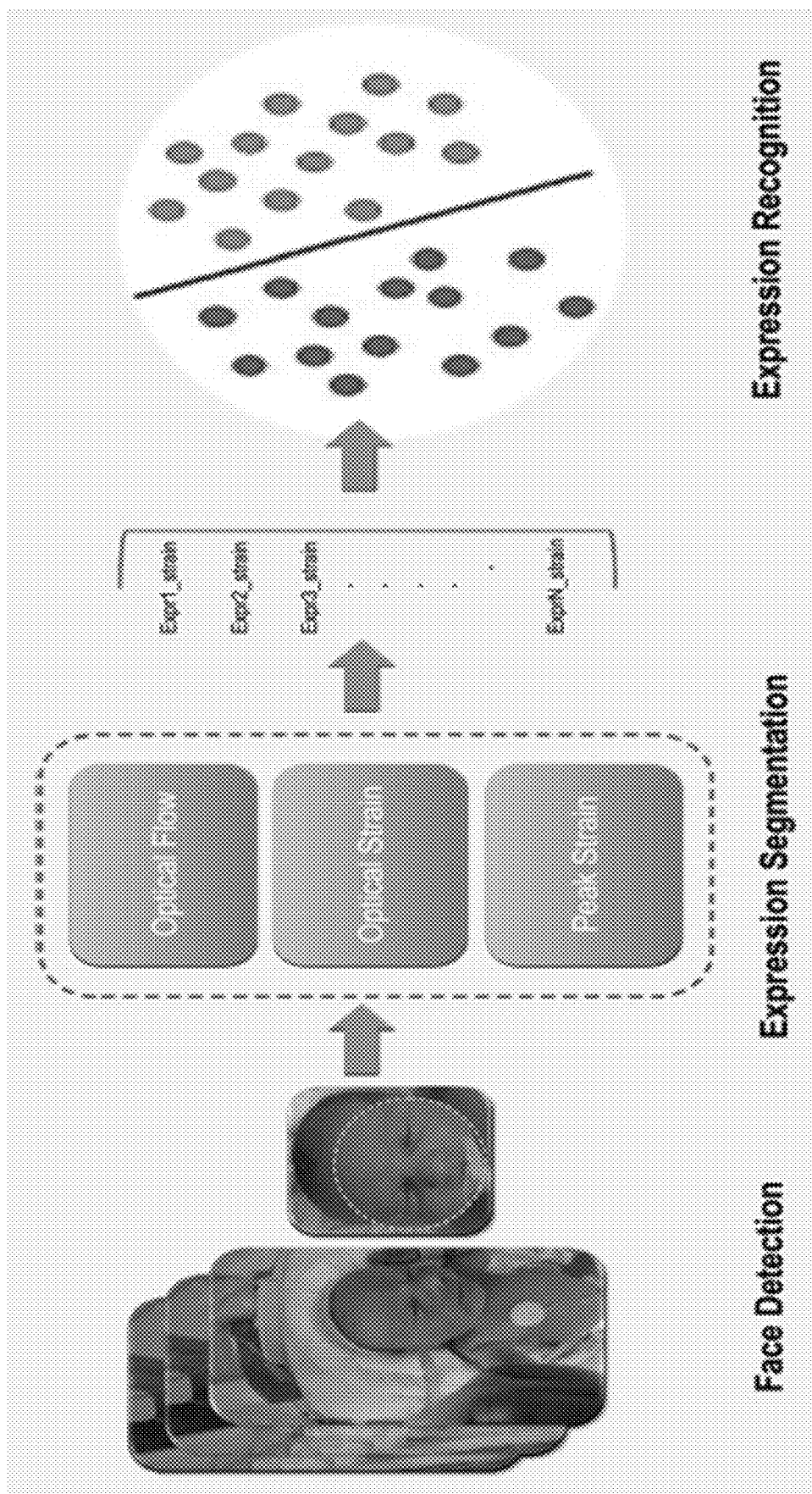
FIG. 5 is an image depicting the three stages of the machine-based infant pain expression recognition system: face detection, expression segmentation and expression recognition/classification.

Shreve et al. [11-13], which are incorporated herein by reference in their entireties, discuss an algorithm to segment any expression in a video sequence by capturing the optical strain corresponding to elastic distortions of facial skin tissue. The facial optical strain can be derived directly from the vectors of optical flow, which is a well-known motion estimation technique based on the brightness conservation principle [20]. The facial strain algorithm can be summarized as follows (also see FIGS. 5 & 8):
- A. Take a video sequence as input and locate sixty-six facial points in each frame. These points are used to align the face, crop it, and divide it into four regions.
- B. Generate an optical flow vector for each region of the face over all frames and use this vector to estimate the optical strain.
- C. Add the estimated strain values for each region together to generate the overall strain magnitude.
- D. Apply a peak detector to detect the points of maximum strain magnitude, which correspond to facial expressions.

Figure 8:
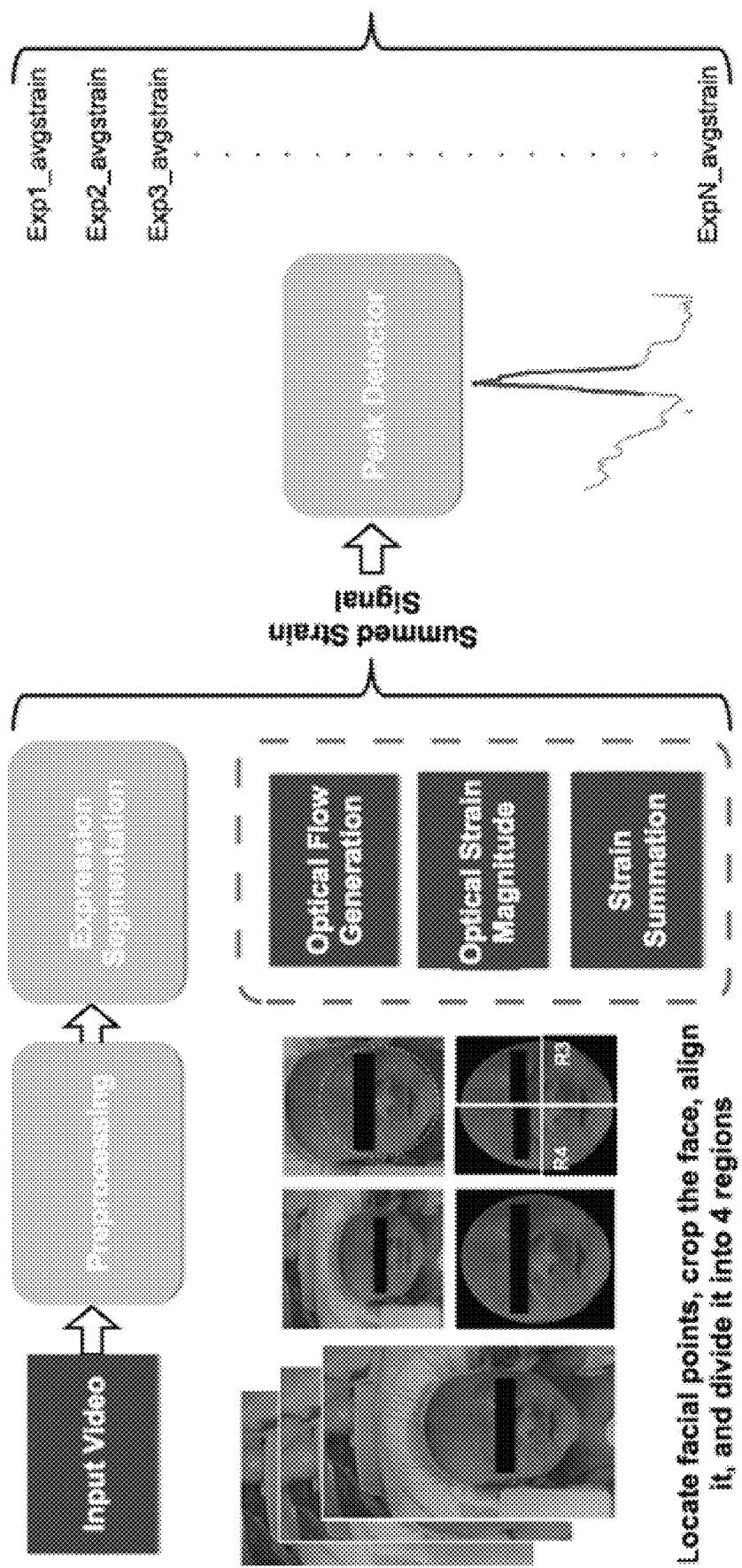
FIG. 8 is an overview of pain expression algorithm based on facial strain analysis, according to certain embodiments of the current invention.

FIG. 8 presents a block diagram of the segmentation algorithm [13]. The results of applying this algorithm on video sequences of infants will become clearer as this specification continues.

E. Classification

The strain magnitude is a primary feature used to classify the expression as pain or no-pain. The expression-segmentation algorithm, described previously, generates a strain value for each frame of the segmented expression. A representative single strain value for the entire expression is then computed by taking the average of strain values over all frames of the expression. To classify the segmented expression, two classifiers k Nearest-Neighbor (KNN) and support vector machine (SVM) are employed.

Experiments

A. Expression Segmentation

Figure 7:
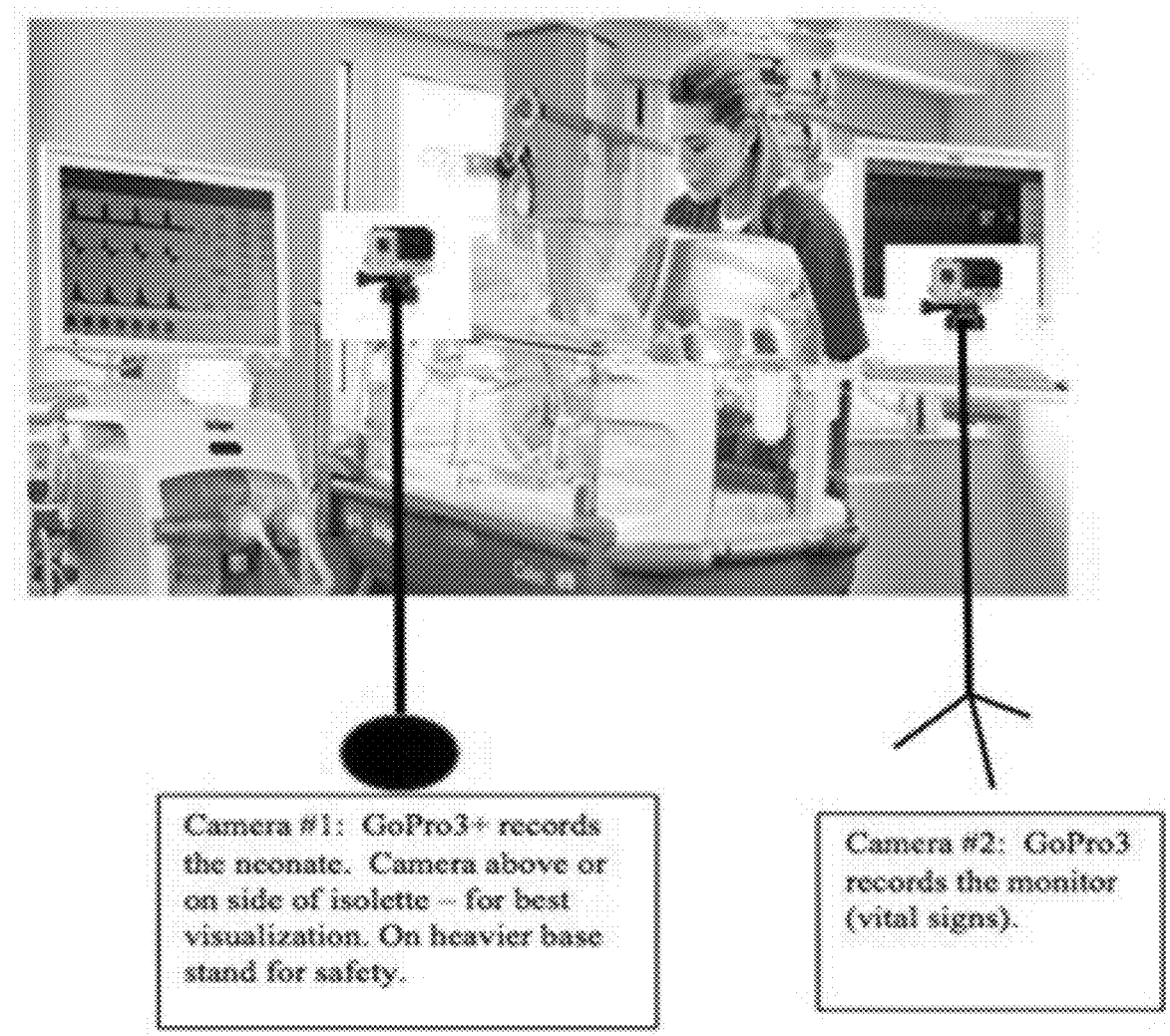
FIG. 7 is an illustration of the recording setup and equipment, according to certain embodiments of the current invention.

The segmentation algorithm is applied on a set of video sequences of the pain procedure to extract the strain magnitude value of each frame. The peak detector method then segments the expression by finding the points of maximum strain. Each of these segmented expressions is represented by a single strain value, as mentioned earlier. FIG. 7 shows the result of running the algorithm for an infant with acute pain. As can be seen in the figure, the algorithm does not generate continuous expression segmentation. This may happen because infants usually do not experience acute pain when the procedure starts by insertion of the lancet in the heel; the acute pain occurs during the squeezing events [21].

Figure 4:
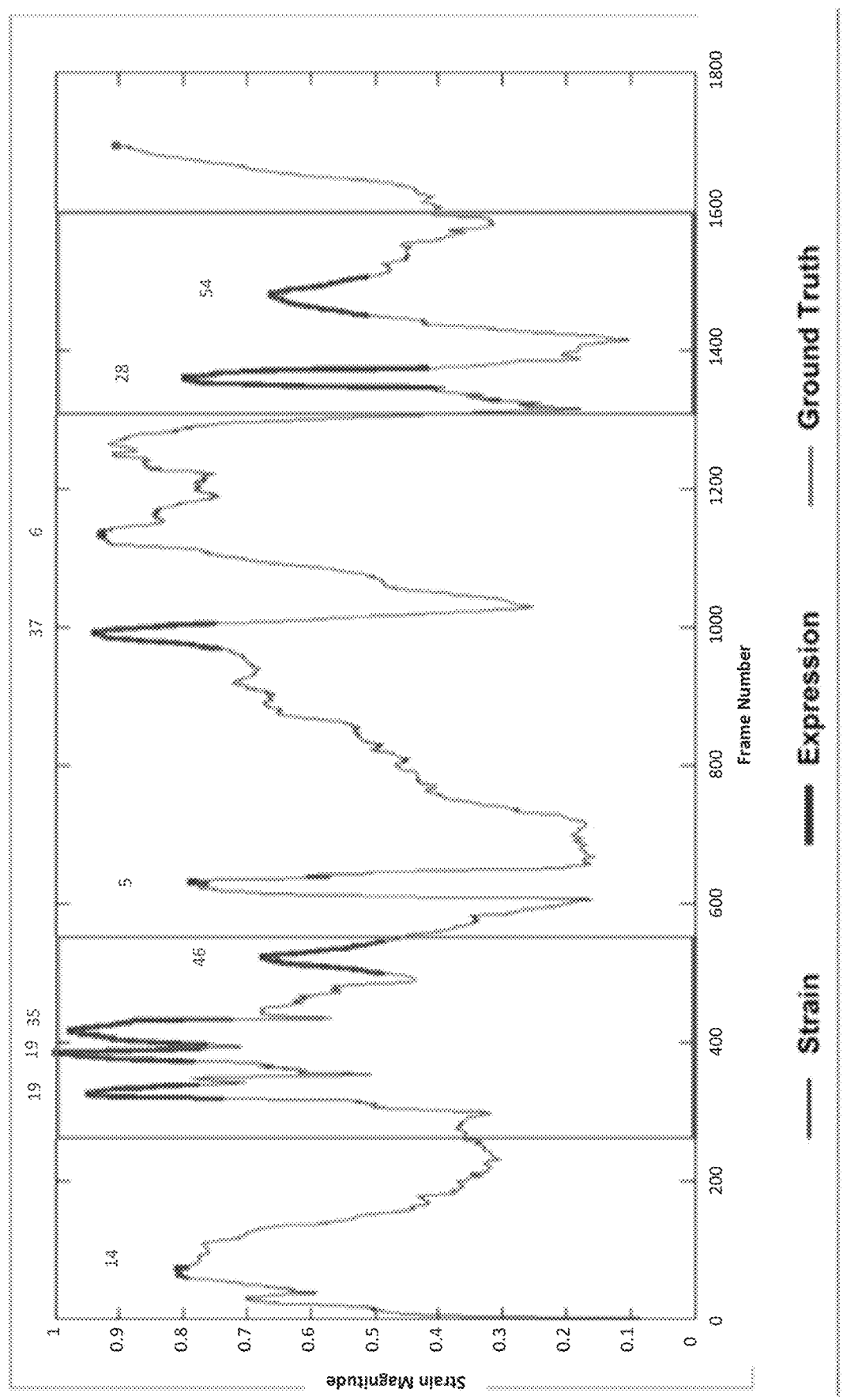
FIG. 4 is a graphical illustration depicting the results of expression segmentation testing. The accuracy of correctly recognizing the expression as pain for KNN and SV vi classifiers was 96% and 94%, respectively. The blue line represents the strain value; the thick blue line represents the segmented expression; the number above the curve represents the number of frames that belong to the expression; and the red dashed line represents the start and end of the pain procedure.

The area under the Receiver Operating Characteristic curve (ROC) was adopted as a measure of performance for expression segmentation algorithm. The ROC, which is shown for 10 subjects in FIG. 3, achieves 80% True Positive Rate (TPR) with a 20% False Positive Rate (FPR), and has a peak of 97% TPR with less than 60% FPR. High FPR can be attributed to the segmentation algorithm classifying any facial motions (e.g., sucking on the pacifier) as expression. As can be seen in FIG. 4, the algorithm segmented the infant's facial motion of sucking as expression. Alternatively, high FPR can be attributed to a failure in optical flow computation and strain estimation as a result of strong and out-of-plane head movements.

B. Expression Recognition or Classification

Video sequences of seven (7) subjects were used for training and videos of three subjects were used for testing (i.e., unseen data). For expression classification, KIN classifier in WEKA (Waikato Environment for Knowledge Analysis) [23], which is JAVA machine learning software, was used with different values of k to classify the segmented expressions as pain or no-pain. The accuracy of the correctly classified instances was 96% with k=3. SVM (LIBSVM in WEKA) was also used for classification, and the accuracy for correctly classified instances was approximately 94%. This promising accuracy was obtained by utilizing the strain as a single feature for classification. Building a multi-class pain classifier by utilizing other features in addition to the strain is thus contemplated and described herein.

Development of Multimodal Pain Assessment System

It is an object of certain embodiments of the current invention to develop a multimodal pain assessment system that aims to:
1. Monitor infants and detect signs that are associated with pain (e.g., pain expression, crying, body motion and vital signs) when the infants are left unattended; and
2. Generate a minimally biased total pain score based on several signs of pain and report this score to a nurse.

In application, this system can provide a consistent and minimally biased pain-scaling tool to be used in the NICU at hospitals, in houses as home-monitoring to check on an infant's condition at all hours, and in developing countries where there is a lack of medical workers/supplies.

It is contemplated herein that with larger datasets, other pain indicators, such as infants' crying, vital signs, and body motion can be utilized in addition to facial expressions. It should be noted that the results presented herein are based on the initial data collection, which has 10 subjects.

Infant Facial Expression

In an embodiment, the current invention is a machine-based infant pain assessment tool, which can monitor infants continuously, detect various pain indicators (e.g., facial expression of pain, crying, body motion and changes in heart rate), and generate a total pain score based on these indicators. The first step of the implementation of this tool has been accomplished by focusing on facial expression of pain as a behavioral indicator of pain, as described previously. As discussed, the model of recognizing infants' facial expression of pain has three main stages: infants' face detection and tracking, expression segmentation; and pain recognition.

A. Stage I—Infants' Face Detection and Tracking

Before analyzing facial expressions, the face is detected and tracked in video frames. There are several known face detection algorithms that can detect and track faces with high accuracy. However, as noted previously, most of these algorithms perform well in detecting adult faces, but fail in case of infants. In light of these difficulties, in certain embodiments of the current invention, the described infant face detection model was developed using the Adaptive Boosting algorithm, and the model was trained based on the dataset described herein. Other suitable face tracking algorithms may be used in the current invention as well.

The general steps performed to build the haar-cascade training model for analyzing infant facial expressions is described below. It is noted that this training model is an example implementation, and other known, suitable implementations for face tracking are contemplated by the current invention as well.

First, the image samples were prepared and were used to train the model. The image samples were divided into positive and negative image samples. Positive image samples contained the desired object to be detected, specifically the infants' faces here. Negative image samples were arbitrary images that did not contain the desired object (the infants' faces) to be detected. For example, 1,000 positive images containing infants' faces with different orientations were used, along with 2,000 negative images of the background without infants' faces.

Second, after preparing the images, the classifier was trained to distinguish between positive images (face) and negative images by building the hair-cascade classifier using C++ and Open CV. The classification learning process requires a set of positive and negative images for training, and a set of features (haar-like features) were selected using AdaBoost (adaptive boosting) for training the classifier. To improve the learning performance of the algorithm (which is sometimes called a weak learner), the AdaBoost algorithm can be used. AdaBoost provided guarantees in several procedures. The process of "boosting" works with the learning of single simple classifier and rewriting the weight of the data where errors were made with higher weights.

Afterwards, a second simple classifier was learned on the weighted classifier, and the data was re-weighted on the combination of the first and second classifier and so on until the final classifier was learned. Therefore, the final classifier was the combination of all previous n-classifiers. The AdaBoost cascade of classifiers was seen as a robust method of detection and characterization.

Finally, the trained model was tested using some unseen data (i.e. new images that were not used for training). The model outputs "1" and draws a rectangle around the detected region if it is a face, and outputs "0" if a face is not detected.

B. Stage II—Expression Segmentation

Matthew's algorithm was used to segment facial expression dynamically based on facial strain analysis. It should be noted here that Matthew's original work was evaluated with the six standard expressions (e.g., happiness, anger, disgust, surprise, fear, and sadness) and with the less challenging dataset of adults. The current algorithm was evaluated with a pain expression and with a more challenging dataset of infants.

C. Stage III—Pain Recognition

Machine learning algorithms (e.g., support vector machine) were used to classify the segmented expression as pain expression (1) or other expressions (0).

Other pain indicators—for example infants' crying, vital signs, and body motion—can also be used to build a pain assessment tool with the ability to generate a total pain score based on various indicators, where each of these indicators generates a score that contributes to the total pain score.

i. Infant Cry

To utilize an infant's crying as a pain indicator, a method was developed to recognize infants' emotions (e.g., pain, hunger) expressed in their crying based on frequency and pitch analysis of crying signals. The development of the method begins by performing preprocessing operations such as filtering out the noise and deciding the window size. Subsequently, frequency-based features, such as fast Fourier transform or Mel-frequency coefficients, are extracted to represent audio segments. These features are used subsequently to train and build a crying recognition classifier. Speech signal analysis is contemplated herein as well to recognize infants' emotions expressed in their crying.

ii. Infant Vital Sign

Vital signs, including, but not limited to, heart rate, breathing rate, and oxygen saturation rate, measure the physical condition of an infant's body. For example, studies have shown that there is a strong correlation between an infant's pain intensity and an increase in the infant's heart rate. method was developed herein to analyze sequences of vital signs and determine whether a specific sequence correlates to pain based on score function. For example, to predict whether a sequence of heart rate corresponds to pain, a score for each frame in the sequence is generated, and the sum of these scores gives a total score for the entire sequence. This total score corresponds to pain if it exceeds a predetermined threshold. Other parametric and non-parametric classifiers are contemplated herein and may also be used to quantify and score vital signs.

iii. Infant Body Movement

Infants tend to move their arms and/or legs when they experience pain. Thus, it may also be important to utilize infants' body motion as pain indicator. The infants' motions are analyzed and used to detect motions corresponding to pain.

Use of Multimodal Pain Assessment System

As contemplated herein, the instant pain score generator system/methodology/software uses image/video processing and machine learning algorithms to generate both individual pain assessment scores for each parameter and also an overall total pain score, which is a summation and/or weighted balance of the individual pain assessment scores. The generator can be integrated into the infant's incubator system or to a camera or installed as an application in an electronic device such as a smartphone or tablet. The resulting infant's pain assessment tool measures an infant's pain intensity using various indicators, such as facial expression, crying, body motion and vital signs, as described previously.

Figure 6:
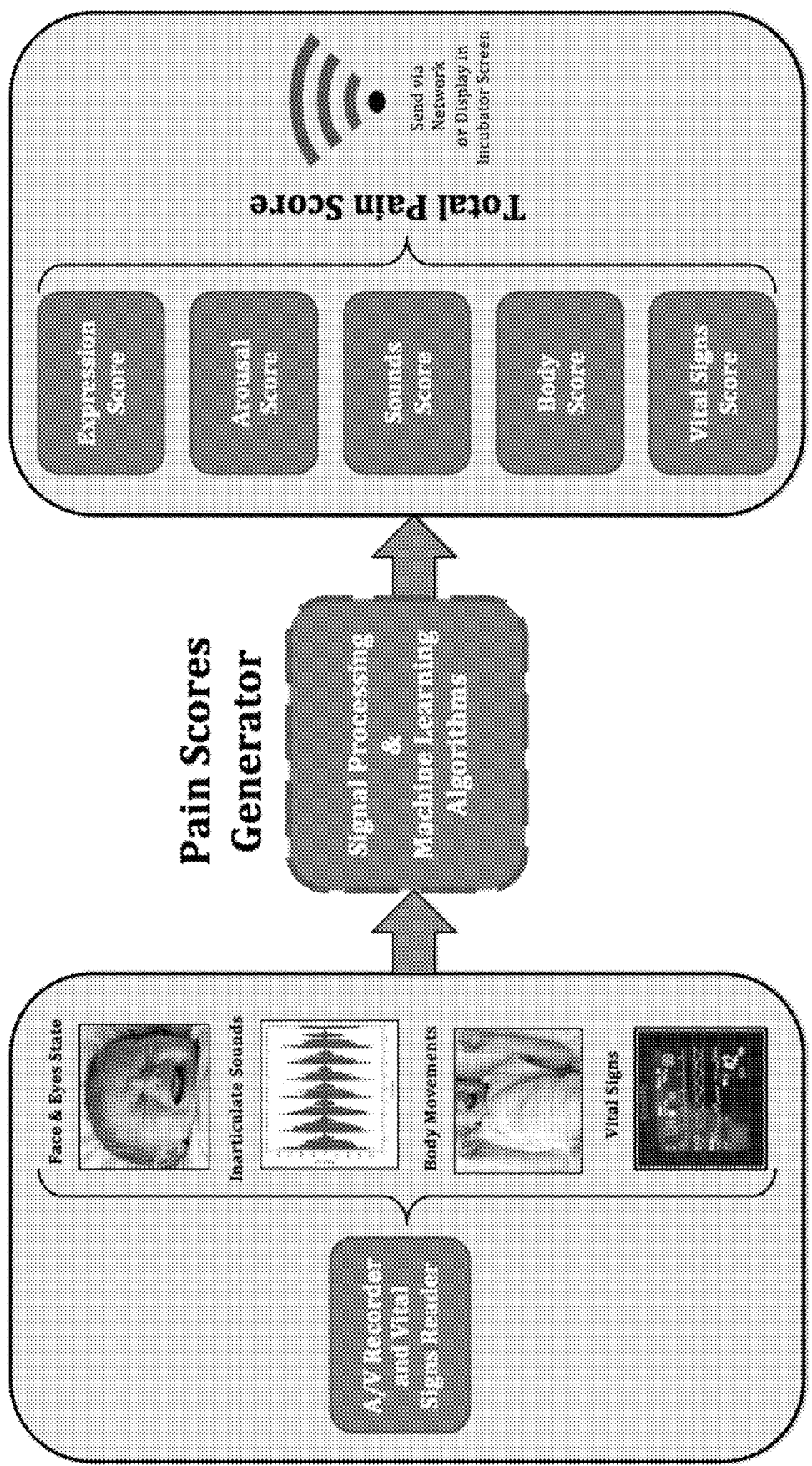
FIG. 6 is an image depicting the components of the infants' pain assessment tool which uses different measures to determine a total pain score. In use, data is acquired of different pain indicators using video, audio, body and vital signs recording. Software is used to process and analyze the acquired data and generate a total pain score by summing up all of the pain scores from the various pain indicators. The generated total pain score is then sent to a remote station via Wi-Fi or alternatively it is displayed in the infant's incubator.

The components of the infant's pain assessment tool are illustrated in FIG. 6. In use, the infant's pain assessment tool employs data readers, for example cameras, microphones or other recorders, to obtain infant data of various pain indicators such as facial expressions, voice, vital signs, and body motion. The data reader can be attached to the incubator itself or to a stand adjacent to or otherwise corresponding to the incubator.

A total or weighted pain score is generated based on the various indicators by utilizing several signal and image/video processing and machine learning algorithms, such as optical flow, facial strain, local binary patterns (LBP), linear predictive coding (LPC), linear regression, neural network, etc. Machine learning classifiers or algorithms were divided into two main categories: parametric (linear regression) and non-parametric (neural network). The total weighted pain score is computed by weighing or summing up a variety of pain scores—such as score of pain expression, score of crying, score of body motion, score of vital signs, and score of state of arousal—though additional suitable categories are contemplated herein as well.

Table II below illustrates five (5) different pain scores. Pain generator software/code can be integrated into the infant's incubator, a camera, etc.

Adding up the score for each parameter, for example, generates a total pain score, The breathing pattern parameter corresponds to the vital signs, and the arms/legs parameter corresponds to body motion.

After the total pain score is generated, the score can be transmitted wirelessly (e.g., Wi-Fi) to a remote station (e.g. a nurse's station, doctor's station, caregiver's smart device, etc.) or can be displayed on the infant's incubator itself.

Example 1

Video and audio data (i.e., video data of face, body, and sounds) along with vital signs data for a total of 43 subjects older than 30 weeks gestational age (e.g., premature and infants) were recorded using cameras (e.g., GOPRO cameras) under two different pain conditions: acute and chronic. Gestational age was calculated from the first day of the mother's last menstrual period. Acute pain recordings were carried out during heel lancing procedures that were previously scheduled for routine blood test in the presence of nurses who scored the pain moments using the NIPS (Neonatal Infant Pain Scale) scoring tool. The scores were taken prior to, at the start, and during the procedure, and at every minute after the completion of the procedure for around five minutes. These scores were used as ground-truth, to validate the results of the instant system and methodology. Infants with chronic pain were monitored during the post-operative recovery for up to three (3) hours in the presence of nurses who scored the pain using the NPASS (Neonatal Pain, Agitation, Sedation Scale) scoring tool prior the surgery (i.e., normal Mate), and every 15 minutes after the surgery and during the chronic pain.

TABLE II

| NPASS (Neonatal Pain, Agitation, Sedation Scale) | | | | | |
|---|---|---|---|---|---|
| Assessment | Sedation | | Normal | Pain/Agitation | |
| Criteria | −2 | −1 | 0 | 1 | 2 |
| Crying Irritability | No cry with painful stimuli | Moans or cries minimally with painful stimuli | Appropriate crying Not irritable | Irritable or crying at intervals Consolable | High-pitched or silent-continuous cry Inconsolable |
| Behavior State | No arousal to any stimuli No spontaneous movement | Arouses minimally to stimuli Little spontaneous movement | Appropriate for gestational age | Restless, squirming Awakens frequently | Arching, kicking Constantly awake OR Arouses minimally/no movement (not sedated) |
| Facial Expression | Mouth is lax No expression | Minimal expression with stimuli | Relaxed Appropriate | Any pain expression intermittent | Any pain expression continual |
| Extremities Tone | No grasp reflex Flaccid tone | Weak grasp reflex ↓ muscle tone | Relaxed hands and feet Normal tone | Intermittent clenched toes, fists, or finger splay Body is not tense | Continual clenched toes, fists, or finger splay Body is tense |
| Vital Signs HR, RR, BP, SaO$_2$ | No variability with stimuli Hypoventilation or apnea | <10% variability from baseline with stimuli | Within baseline or normal for gestational age | ↑ 10-20% from baseline SaO$_2$ 76-85% with stimulation-quick recovery ↑ | ↑ >20% from baseline SaO$_2$ ≤75% with stimulation-slow recovery ↑ Out of sync with vent |

A. Participants

Forty-three infants, older than 30 weeks gestational age (e.g., premature and newborn), were videotaped in the NICU at Tampa General Hospital. Exclusion criteria included infants with facial abnormality or gestational age less than 30 weeks. Prior to data collection, informed consent was obtained from each infant's parents. The procedure for collecting the data complied with the protocols and ethical directives for research involving human subjects at the University of South Florida.

The average age of the recorded infants was around 37 weeks gestational age (min: 30 weeks, max: 41 weeks). Thirty infants were non-Hispanic, and 13 infants were Hispanic. Infants were recorded under two different pain conditions: acute and chronic pain. Thirty-four infants were recorded during acute pain procedure, seven infants were recorded during both chronic pain and acute pain, and two infants were recorded during chronic pain procedure. Acute pain recordings were carried out during immunization or heel sticking procedure, which had been previously scheduled for routine blood test. The infants with chronic pain were recorded during the post-operative recovery for up to 3 hours in the presence of nurses who monitored the infants and scored his/her pain experience.

B. Monitoring System Setup

Prior to data collection, the study was explained to each infant's parents, and their permission was obtained by asking them to sign a consent form. Thereafter, the recording equipment—which included cameras (e.g., GOPRO), camera stands, vital signs reader, tablet (e.g., IPAD MINI), subject's identifier sheet, and the scoring sheets—were prepared and brought to the infant's room. Infants were recorded with the cameras at high (e.g., 4K) resolution. The recorded data included video sequences of the infant's face/upper body, audio data of the infant's voice, and data pertaining to the infant's vital signs. Any suitable vital signs reader, such MEDTRONIC VITAL SYNC Virtual Patient Monitoring Platform, can be used for recording a wide range of vital signs data.

The acute pain recording (e.g., immunization or heel-sticking) started by recording the infant for about five (5) minutes in normal state before the pain procedure, during the procedure, and for about (5) minutes after the completion of the procedure in the presence of expert nurses who scored moments of pain. For the chronic pain (e.g., post-operative pain), infants were recorded first in normal state prior the surgery and then after the surgery for up to about three (3) hours in the presence of expert nurses who scored moments of pain.

C. Ground Truth

Two nurses attended the recordings and filled out the ground truth sheets using NIPS (Neonatal Infant Pain Scale) (Table III) and NPASS (Neonatal Pain. Agitation, Sedation Scale) (Table II) pain scales. NIPS is used to scale the acute pain and NPASS is used to scale the chronic pain. The NIPS pain scale has binary ranges for all indicators except crying. The NPASS pain scale ranges from −2 to 2.

TABLE III

NIPS Pain Scale (Neonatal Infant Pain Scale).
A sum of the points is obtained.

| Parameter | Finding | Points |
| --- | --- | --- |
| Facial Expression | Relaxed | 0 |
| | Grimace | 1 |
| Cry | No cry | 0 |
| | Whimper | 1 |
| | Vigorous crying | 2 |
| Breathing Pattern | Relaxed | 0 |
| | Change in breathing | 1 |
| Arms | Relaxed | 0 |
| | Flexed/extended | 1 |
| Legs | Relaxed | 0 |
| | Flexed/extended | 1 |
| State of Arousal | Sleeping/awake | 0 |
| | Fussy | 1 |

Expert nurses in two (2) different conditions, the initial real life scores and the short-video episodes scores, took the ground truth scores by rating the infant pain experience. A nurse, who attends the pain procedure and observes signs of pain, fills out the initial scores. Each acute recording has a total of 7 ground truth scores, which were collected prior to the pain procedure, at the start of pain procedure, and at every minute for around five (5) minutes after the pain procedure is completed. The ground truth for the chronic pain was taken every fifteen (15) minutes prior the surgery in the normal state and every fifteen (15) minutes after the surgery and during the chronic pain.

For short-video episodes, four expert nurses watched these videos of the pain procedure individually and scored them. The length of video episodes was five (5) seconds and ten (10) seconds for acute pain and chronic pain, respectively.

Experiments are conducted to measure the subjectivity of pain scores between different observers. For examples, differences between an observer's initial scores and the same observer's video episodes scores or the variability of ground truth scores among four different observers.

This dataset is challenging because infants tend to make unpredictable movements (i.e. infants make different and strong out-of-plane head movements). In addition, self-occlusion by hand or occlusion by external items such as a pacifier, toys, or tapes make the dataset challenging as well as low lighting conditions.

Example 2

As discussed herein, an embodiment of the current invention is a multimodal computer-aided pain assessment tool for use in preterm and term infants. While the prior art demonstrated the relationship between isolated behavioral and physiologic changes and infant pain, a pain assessment tool is needed that allows for the automated integration of infants' facial strain patterns, body motion, crying sounds, and vital signs. This pain assessment tool is enabled herein. This integrated data (infants' facial strain patterns, body motion, crying sounds, and vital signs) was evaluated in comparison with validated nurse-generated pain scores to perform multivariate regression analysis and establish pain inference models that can assess pain using the identified indicators.

An objective is to demonstrate that computer-aided pain assessment provides a sensitive and consistent assessment of infant pain similar to the traditional nurse scoring. The computer-aided pain assessment is accomplished with a cost-effective system based on video cameras and image; signal processing algorithms. This diagnostic tool improves the assessment of pain in infants, and helps guide treatment by generating a more consistent and objective pain assessment.

A. Preliminary Approach i. Preliminary Data Collection

Preliminary studies on premature and term infants were performed in the NICU at Tampa General Hospital (TGH). The procedure of collecting the data complied with the protocols and ethical directives for research involving human subjects. A total of 43 infants were videotaped during acute episodic and prolonged acute painful procedures. Prior to video recording, informed consent was taken from the infant's parents. FIG. 7 is an illustration of the recording setup and equipment.

For the acute episodic pain assessments, thirty-four infants were videotaped during brief skin lancing procedure (e.g., heel lancing and immunization) in the presence of two trained nurses who assessed their pain using the NIPS pain scale. The infants were recorded for five minutes prior the procedure to determine their baseline state of arousal and pre-procedure NIPS score. The NIPS score was documented again at the start of the procedure and then every minute for five minutes after the procedure was completed. NIPS assessments were time stamped on the recorded video for synchronization with the automated scores.

For the prolonged acute pain assessments, a total of nine (9) infants were recorded during the post-operative period (laparotomy, gastrostomy tube placement) for approximately three (3) hours in the presence of two trained nurses. The nurses assessed the infants using NPASS pain scale at the start of the recording after observing the infant and then every 15 minutes during the evaluation period. NPASS assessments were time stamped on the recorded video for synchronization with the automated scores.

ii. Pain Detection Based on Facial Strain

Based on the initial data collection, a novel process was developed for assessing infant pain on video sequences by utilizing infants' facial expressions. This methodology includes three main stages: (1) detection of the infant's face in a video sequence followed by preprocessing operations including face alignment; (2) expression segmentation based on facial strain analysis; and (3) expression recognition and classification. Manual detection of infants' faces was performed to extract facial points. A strain algorithm was employed to segment expressions by exploiting the non-rigid facial motion that occurs during facial expression; FIG. 8 presents an overview of this methodology. The accuracy of classifying the segmented expressions as pain or no pain using k Nearest Neighbor (KNN) and support vector machine (SVM) were 96% and 94%, respectively.

Table IV shows the confusion matrix of a KNN classifier. The confusion matrix, which is used to measure the classifier's performance, is a matrix that has information about the actual (column) and predicated (row) classifications acquired by a specific classifier. The results of the current methodology indicate that dynamic analysis of facial expression in infants can be used to assess pain.

TABLE IV

Confusion Matrix of KNN. N represents the total number of instances. The first row of the matrix represents the predicted class and the first column represents the class of actual ground truth. For instance, the KNN classifier was able to correctly classify 28 pain instances as pain and misclassify one instance of pain as no pain.

| | | Classifier Prediction | | |
|---|---|---|---|---|
| N = 67 | | Pain | No Pain | Total |
| Ground Truth (Actual) | Pain | 28 | 1 | 29 |
| | No Pain | 2 | 36 | 38 | iii. Pain Detection Based on Sound Analysis

Figure 9:
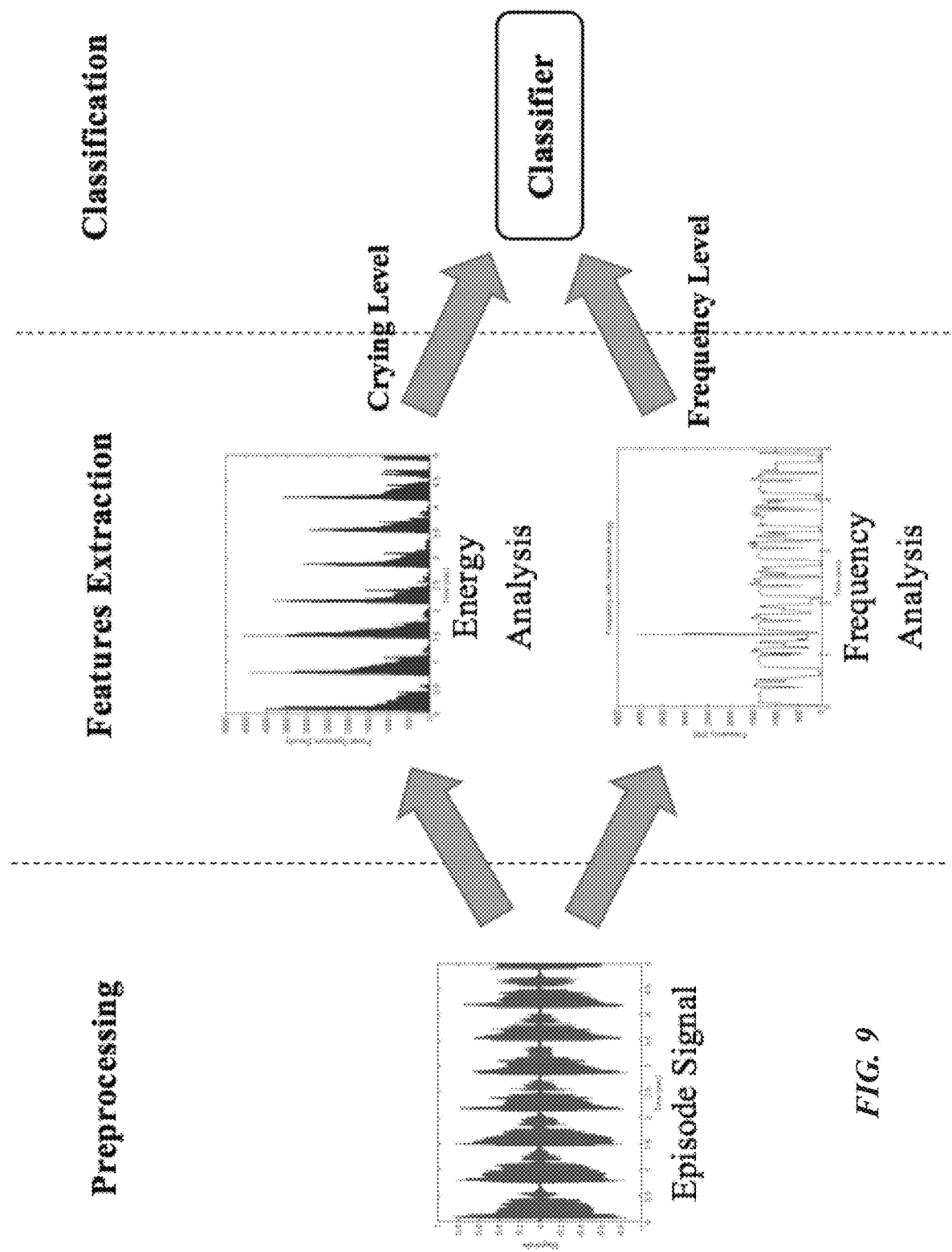
FIG. 9 is an illustration of the pain detection method based on infants' sounds analysis, according to certain embodiments of the current invention.

To classify infant crying as it pertains to infant pain, a method was developed and includes three main stages: preprocessing stage, features extraction stage, and classification stage. In the preprocessing stage, the entire audio signal is segmented into pain/no-pain episodes based on the given ground truth. In the features extraction stage, a set of features (e.g., crying level and frequency level) is extracted from the segmented episodes based on energy and frequency analysis. In the classification stage, the extracted features of each episode are classified into one of three classes: no cry (class 0), whimper (class 1); and vigorous crying (class 2). The accuracy of classifying the crying sounds based on simple thresholding was approximately 88%. FIG. 9 illustrates the stages of this method, and Table V shows the confusion matrix of the classification stage.

TABLE V

Confusion Matrix.

| | | Classifier Prediction | | | |
|---|---|---|---|---|---|
| N = 49 | | Class 0 | Class 1 | Class 2 | |
| Ground Truth (Actual) | Class 0 | 34 | 2 | 0 | 36 |
| | Class 1 | 0 | 3 | 1 | 4 |
| | Class 2 | 1 | 2 | 6 | 9 | iv. Pain Detection Based on Vital Signs Analysis

Vital signs measurements have been collected in the current study for infants under different pain characteristics (i.e., isolated and prolonged acute pain). Specifically, vital signs data (i.e., heart rate (HR), respiratory rate (RR), and oxygen saturation ($SpO_2$)) for a total of 18 infants were collected to ascertain the correlation between these measurements and infants' pain experience using machine-learning algorithms.

Figure 10:
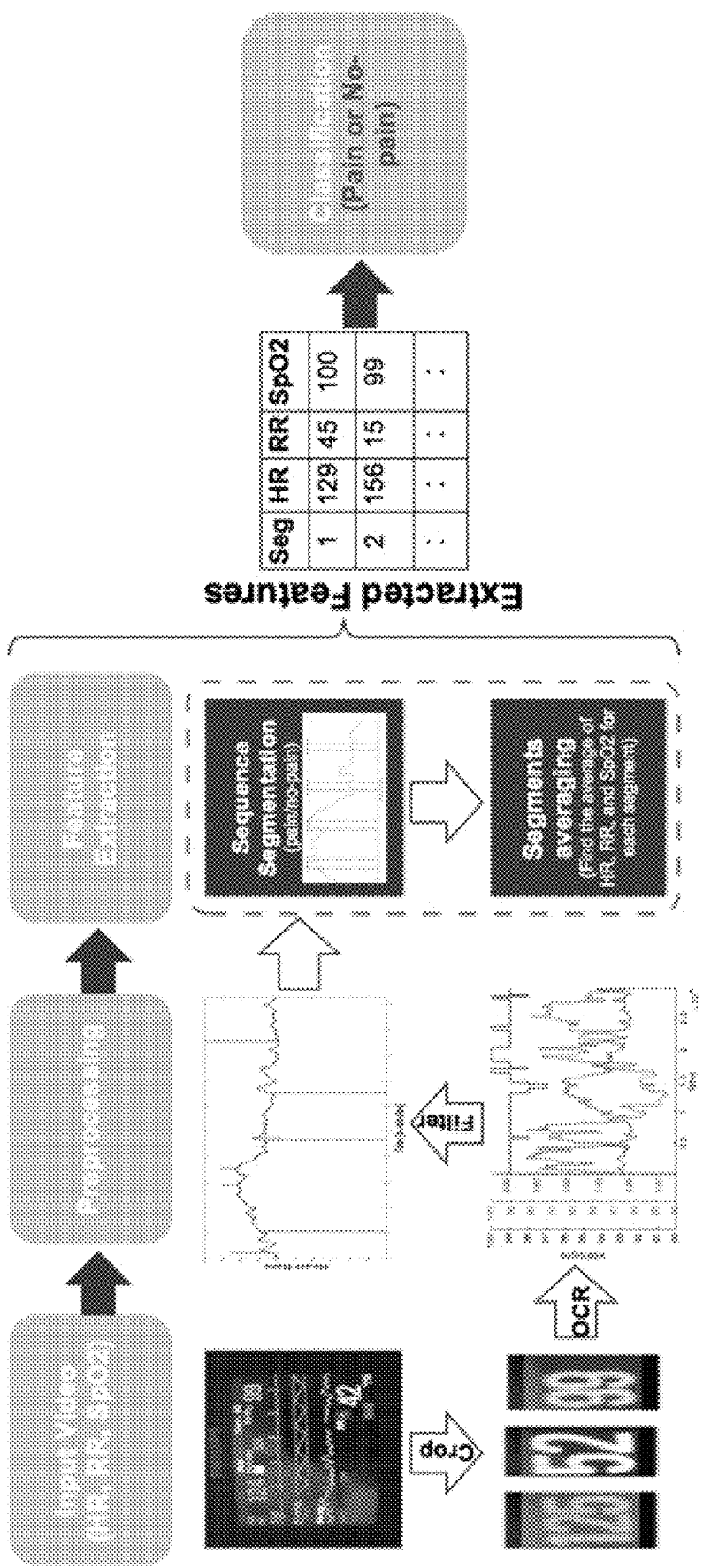
FIG. 10 is an illustration of the pain detection method based on infants' vital signs analysis, according to certain embodiments of the current invention.

The method to assess infant pain based on vital signs analysis includes three main stages: preprocessing stage, feature extraction stage, and classification stage. In the preprocessing stage, in which optical character recognition (OCR) is performed, the videotaped vital signs frames are transferred into sequences of digital numbers; a median filter is then applied to these sequences to exclude the outliers. In the feature extraction stage, the filtered sequences are segmented into pain/no-pain episodes based on the given ground truth. The features of each episode are then extracted by taking the average of that episode. In other words, three features (HR, RR, and $SpO_2$) were extracted for each episode. In the classification stage, the extracted features are classified as pain (1) or no-pain (0) by utilizing different machine learning classifiers; the accuracy of classifying this stage based on tree classifier (i.e., random forest) was found to be about 97% (accuracy was increased by extracting the outliers instances and applying more than one trees (forest of trees)). A depiction of these three stages is presented in FIG. 10, and Table VI shows the confusion matrix.

TABLE VI

Confusion matrix.

|  | Pain | No-pain |
|---|---|---|
| Pain | 65 | 0 |
| No-pain | 4 | 61 | v. Pain Detection Based on Other Indicators

The infants' body motions may also correspond to pain and can be measured by applying well-known motions estimation algorithms, such as optical flow, block matching, and pixel tracking algorithms.

Correlating pain with the infant's state of arousal is also contemplated herein. State of arousal is defined as the state of being fussy or relaxed during pain stimuli. The score of this indicator is given by observing the eyes motion (e.g., eyes continually shut or open), speed of the breathing, and arms motions). Several eye-blinking detections and arms motions algorithms, along with the speed of infant breathing, can be applied to automate this process.

B. Objectives

Figure 11:
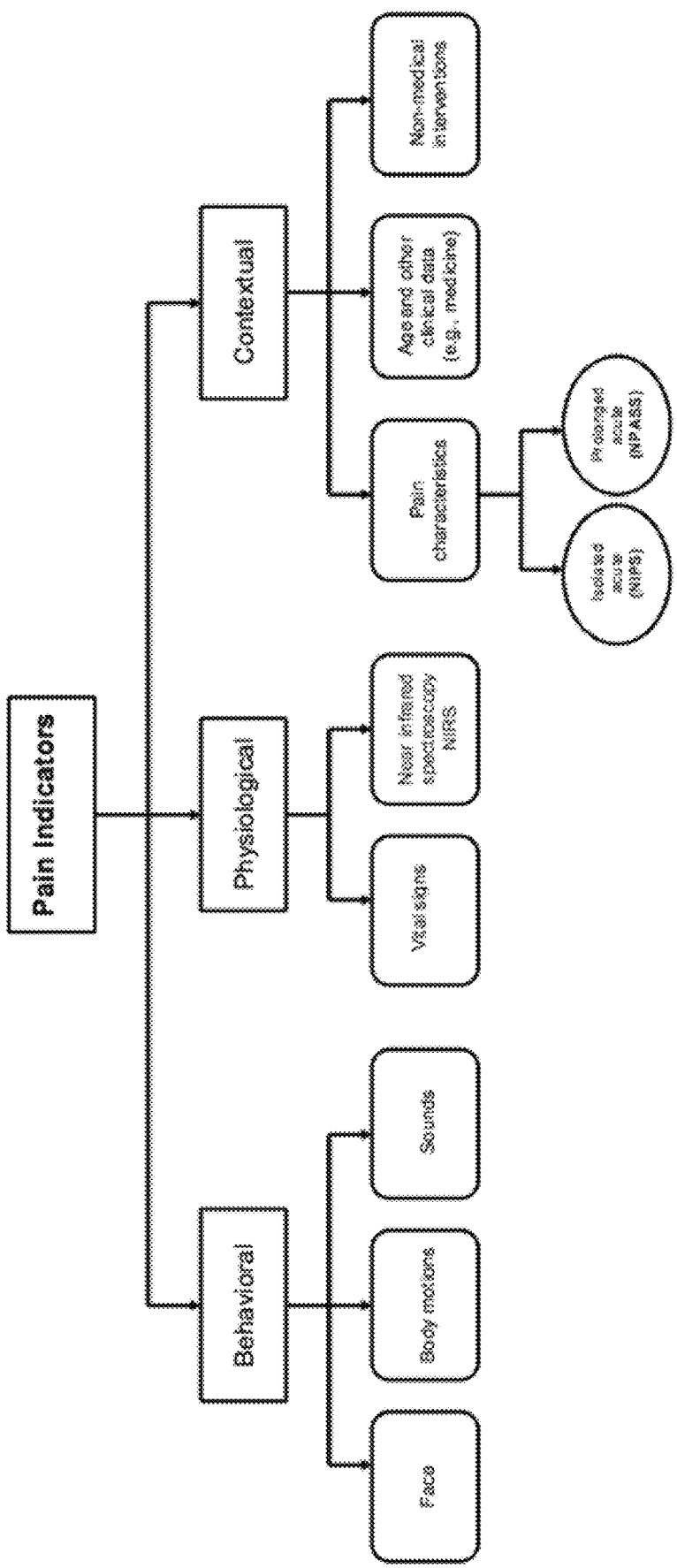
FIG. 11 is a diagram of the pain indicators, according to certain embodiments of the current invention.

An objective of the current study is to build an automated infant pain assessment system that simulates the nurses' task in assessing infant pain at the NICU. Specifically, this system includes a tool that monitors infants and observes signs of pain by taking into account various pain indicators [24, 25], as seen in FIG. 11.

A behavioral indicator is considered and includes the following:
Facial pain indicators such as lowered brows, tightly closed eyes, opened mouth, raised cheeks, and broadened nose.
Body motion pain indicators such as flexed or extended arms/legs, diffuse squirm, finger splay, stretch/drown, grasping, hand in mouth, and fisting.
Sounds such as whimper, moans, and high-pitched crying.
A physiological is considered and includes the following:
Vital signs such as heart rate (FIR), respiratory rate and pattern (RR), saturation rate ($SpO_2$), and the blood pressure (BP).
Near infrared spectroscopy (NIRS) readings.
A contextual indicator is considered and includes the following:
Pain characteristics such as isolated acute pain and prolonged acute pain. Each of these pain types has different measurements and pain scales [26, 27]; thus, this parameter can be used to partition the pain assessment system into two different pain models: isolated acute pain model and prolonged acute pain model.
Gestational age (GA) and day of life age. This indicator may be important since the infants' reaction to pain procedures can vary based on their age.
Clinical data such as medication type and dose, weight/length, race/ethnicity, and gender.
Non-medical interventions such as the mother's presence, rubbing, and the pacifier.
Several studies [28-32] have found associations between the infants' age and their reaction to pain; the most premature infants have limited ability to behaviorally or physiologically respond to painful procedures. Thus, extra points can added to their pain score, based on their gestational age, as compensation for their limitation. Due to this fact; the infants (i.e., samples) can be grouped into four different groups based on their gestational age; these groups, as mentioned above, should be isolated and treated separately.

To develop a system that has the ability to assess pain for different infants' population, the automated infant pain assessment system can be partitioned into two different models based on the pain characteristics: isolated acute pain model and prolonged acute pain model. Each of these models can have its own pain scale and four different groups generated based on infants' group. Both the isolated and prolonged acute pain models can be formulated mathematically as a multivariable regression model. The box diagrams in FIGS. 12A-12B provide a mathematical formulation of these pain models. As can be seen, $X_{1:5}$ represents the feature vectors for each of the pain indicators (i.e., predictors of the regression model). Each of these vectors has its own weight that varies from one group to another based on the infant age. For instance, infants of Group 1 may have difficulty expressing their pain through behavioral pain indictor; more weight should be added in this case to physiological pain indictors. Finally, the total pain score $Y_p$, which represents the response value of the regression model, is used to assess the pain by comparing $Y_r$ to a predetermined threshold. If the total pain score exceeds the given/predetermined threshold, a corresponding therapy or intervention is indicated by the system.

REFERENCES

[1] Hicks, Carrie L., et al. "The Faces Pain Scale—Revised: toward a common metric in pediatric pain measurement." Pain 93.2 (2001): 173-183.

[2] Cornelius, Randolph R. The science of emotion: Research and tradition in the psychology of emotions. Prentice-Hall, Inc., 1996.

[3] Petroni, Marco, et al. "Identification of pain from infant cry vocalizations using artificial neural networks (AVNs)." SPIE's 1995 Symposium on OE/Aerospace Sensing and Dual Use Photonics. International Society for Optics and Photonics, 1995.

[4] Lindh, Viveca, Urban Wiklund, and Stellan Hakansson. "Heel lancing in term newborn infants: an evaluation of pain by frequency domain analysis of heart rate variability." Pain 80.1 (1999): 143-148.

[5] Brahnam, Sheryl, et al, "Machine recognition and representation of neonatal facial displays of acute pain." Artificial intelligence in medicine 36.3 (2006): 211-222.

[6] Brahnam, Sheryl, et al. "Machine assessment of neonatal facial expressions of acute pain." Decision Support Systems 43.4 (2007): 1242-1254.

[7] Brahnam, Sheryl, Loris Nanni, and Randall Sexton. "Introduction to neonatal facial pain detection using common and advanced face classification techniques." Advanced Computational Intelligence Paradigms in Healthcare-1. Springer Berlin Heidelberg, 2007. 225-253.

[8] Brahnam, Sheryl, Loris Nanni, and Randall S. Sexton. "Neonatal Facial Pain Detection Using NNSOA and LSVM." Ipcv. 2008.

[9] Loris Nanni, Brahnam Sheryl, and Lumini Alessandra. "A local approach based on a Local Binary Patterns variant texture descriptor for classifying pain states." Expert Systems with Applications 37.12 (2010): 7888-7894.

[10] Gholami, Behnood, M. M. Haddad, and Allen R. Tannenbaum. "Agitation and pain assessment using digital imaging." Engineering in Medicine and Biology Society, 2009. EMBC 2009. Annual International Conference of the IEEE. IEEE, 2009,

[11] Shreve, M, et al. "Towards macro- and micro-expressions spotting in videos using strain patterns". Workshop on Applications of Computer Vision, December 2009.

[12] Shreve, M, et al. "Macro- and micro-expression spotting in long videos using spatio-temporal strain". International Conference on Automatic Face and Gesture Recognition, number 51-56 c 2012 IEEE, March 2011.

[13] Shreve, M, et al. "Automatic Expression Spotting in Videos", Image and Vision Computing, vol. 32(8), pp. 476-486, 2014.

[14] Anand, K. J. S. "Consensus statement for the prevention and management of pain in the newborn." Archives of pediatrics & adolescent medicine 155.2 (2001): 173-180.

[15] Lawrence, Jocelyn, et al. "The development of a tool to assess neonatal pain," Neonatal network: NN 12.6 (1993): 59-66.

[16] Hummel, P., et al. "N-PASS: Neonatal Pain Agitation and Sedation Scale reliability and validity." Poster presented at: the Pediatric Academic Societies annual meeting. 2003.

[17] Bagnato, Luigi, et al. "Robust infants face tracking using active appearance models: a mixed-state CONDENSATION approach." Advances in Visual Computing, Springer Berlin Heidelberg, 2007. 13-23.

[18] Saragih J. M., Lucey S., and Cohn. J. F. "Face alignment through subspace constrained mean-shifts". In International Conference of Computer Vision, September 2009.

[19] Viola, Paul, and Michael J. Jones. "Robust real-time face detection." international journal of computer vision 57.2 (2004): 137-154.

[20] Beauchemin, Steven S., and John L. Barron. "The computation of optical flow." ACM Computing Surveys (CSUR) 27.3 (1995): 433-466.

[21] Johnston, C. Celeste, and Bonnie J. Stevens, "Experience in a neonatal intensive care unit affects pain response." Pediatrics 98.5 (1996): 925-930.

[22] Kohavi, Ron. "A study of cross-validation and bootstrap for accuracy estimation and model selection." Ijcai. Vol. 14. No. 2. 1995.

[23] Hall, Mark, et al. "The WEKA data mining software: an update." ACM SIGKDD explorations newsletter 11.1 (2009): 10-1.

[24] Holsti, L., et al., Specific Newborn Individualized Developmental Care and Assessment Program movements are associated with acute pain in preterm infants in the neonatal intensive care unit. Pediatrics, 2004. 114(1): p. 65-72.

[25] Craig, K. D., et al., Pain in the preterm neonate: behavioural and physiological indices. Pain, 1993. 52(3): p. 287-299.

[26] Hudson-Barr, D., et al., Validation of the pain assessment in neonates (PAIN) scale with the neonatal infant pain scale (NIPS). Neonatal Network. 21(6): p. 15-21.

[27] Hummel, P. A., et al., Clinical reliability and validity of the N-PASS: neonatal pain, agitation and sedation scale with prolonged pain. Journal of perinatology, 2003. 28(1): p. 55-60.

[28] Valeri, B. O. and M. B. M. Linhares, Pain in preterm infants: Effects of sex, gestational age, and neonatal illness severity. Psychology & Neuroscience. 5(1): p. 11.

[29] Walden, M. and S. Gibbins, *Pain assessment and management: guideline for practice*. Glenview, Ill.: National Association of Neonatal Nurses.

[30] Gibbins, S., et al., Comparison of pain responses in infants of different gestational ages. Neonatology, 2008. 93(1): p. 10-18.

[31] Allegaert, K., et al., *Variability in pain expression characteristics in former preterm infants*. Journal of perinatal medicine, 2005. 33(5): p. 442-448,

[32] Evans, J. C., et al., Longitudinal comparison of preterm pain responses to repeated heelsticks. Pediatric nursing, 2005. 31(3): p. 216.

Paul Viola and Michael J. Jones. Rapid Object Detection using a Boosted Cascade of Simple Features. IEEE CVPR, 2001.

Rainer Lienhart and Jochen Maydt. An Extended Set of Haar-like Features for Rapid Object Detection. IEEE ICIP 2002, Vol, 1, pp. 900-903, September 2002.

Wilson, Phillip Ian, and John Fernandez. "Facial feature detection using Haar classifiers." *Journal of Computing Sciences in Colleges* 21.4 (2006): 127-133.

All referenced publications are expressly incorporated herein by reference, each in its entirety, to the same extent as if each were incorporated by reference individually. Furthermore, where a definition or use of a term in a reference, which is incorporated by reference herein, is inconsistent or contrary to the definition of that term provided herein, the definition of that term provided herein applies and the definition of that term in the reference does not apply.

Hardware and Software Infrastructure Examples

The present invention may be embodied on various computing platforms that perform actions responsive to software-based instructions and most particularly on touchscreen portable devices. The following provides an antecedent basis for the information technology that may be utilized to enable the invention.

The computer readable medium described in the claims below may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any non-transitory, tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wire-line, optical fiber cable, radio frequency, etc., or any suitable combination of the foregoing. Computer program code for carrying out operations for aspects of the present invention may be written in any combination of one or more programming languages, including an object oriented programming language such as Java, C#, C++, Visual Basic or the like and conventional procedural programming languages, such as the "C" programming language or similar programming languages.

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

It should be noted that when referenced, an "end-user" is an operator of the software as opposed to a developer or author who modifies the underlying source code of the software. For security purposes, authentication means identifying the particular user while authorization defines what procedures and functions that user is permitted to execute.

Glossary of Claim Terms

A/V recorder: This term is used herein to refer to a device that receives audio and/or video data. Examples include, but are not limited to, video cameras, sound recorders, etc.

Arousal state: This term is used herein to refer to the condition of the subject's physiological alertness, wakefulness, and attentiveness.

Behavior state: This term is used herein to refer to the condition or pattern of the subject's movements or conduct, and/or the subject's reactions or behaviors during a stimulus.

Body movement classifier: This term is used herein to refer to a module of the system that analyzes and classifies the physical motions of the subject's body into different patterns.

Body movement score: This term is used herein to refer to a value given to the subject's spatial motions upon an automated analysis of those motions, where the score is an indicator of pain felt by the subject.

Data reading device: This term is used herein to refer to any device that is capable of receiving data in the form of audio, video, body measurements, and other pieces of relevant data.

Digital mask: This term is used herein to refer to a digital capture of landmarks on the subject's face. For example, the mask can detect the subject's nose, thus "capturing" the nose, and then can be expanded to include the subject's eyes.

Expression recognition: This term is used herein fir to an identification or observation of the subject's facial motions.

Expression segmentation: This term is used herein to refer to separation out the expression(s) on a subject's face by capturing the optical strain corresponding to elastic distortions of the facial skin tissue.

Extremities tone: This term is used herein to refer to the general condition of the subject's arms and legs. For example, the subject's arms/legs can be stretched out and tight, flexed, curled up, relaxed, etc.

Facial detection: This term is used herein to refer to computer technology that is capable of recognizing or identifying the subject's face from digital images or video.

Facial expression classifier: This term is used herein to refer to a module of the system that analyzes the facial movements/motions of the subject.

Facial expression score: This term is used herein to refer to a value given to the subject's facial movements/motions upon an automated analysis of those movements/motions, where the score is an indicator of pain felt by the subject.

Facial expressions: This term is used herein to refer to any movement or motion of the muscles beneath the skin of the face of the subject.

Facial strain: This term is used herein to refer to the tightness of the muscles of the subject's face.

Frequency-based features: This term is used herein to refer to the characteristics of sounds that relate to the frequency of those sounds, so that the characteristics can be extracted and analyzed.

Inarticulate sounds: This term is used herein to refer to noises made by the subject, where the noises are not expressed in normal words/language, such that there is no immediate clarity of the message based on the noises made.

Landmarks: This term is used herein to refer to recognizable features on the subject's face. An example is the subject's nose, perhaps because it protrudes out of the face.

Machine learning algorithm: This term is used herein to refer to the function behind recognizing particular patterns and applying artificial intelligence to make predictions from a given set of data.

Motions corresponding to pain: This term is used herein to refer to spatial movement of the subject's body, in particular the subject's extremities, Output device: This term is used herein to refer to any apparatus that can transmit a particular finding, conclusion, or data to a user or operator thereof.

Overall strain magnitude: This term is used herein to refer to the level or extent of tightness of the muscles of the subject's face.

Pain intensity: This term is used herein to refer to the strength of an unpleasant sensation experienced by an individual or subject.

Peak detector: This term is used herein to refer to a function that segments the subject's facial expressions by finding the points of maximum strain.

Physical condition: This term is used herein to refer to the state of the subject body's basic functions. Examples include, but are not limited to, heart rate, respiratory rate, oxygen saturation, temperature, etc.

Subject that is incapable of clearly orally communicating said pain intensity or that is capable of communicating said pain intensity through only a behavioral indicator: This term is used herein to refer to an individual who cannot physically speak or otherwise communicate pain in a manner that is absolutely clear to another individual. For example, an infant cannot speak or otherwise clearly communicate pain, other than by using behavior, such as body motions, vital signs, crying, etc.

Vital signs classifier: This term is used herein to refer to a module of the system that analyzes the physical condition of the subject.

Vital signs reader: This term is used herein to refer to any device that is capable of receiving data about vital signs of a subject or individual.

Vital signs score: This term is used herein to refer to a value given to the subject's physical condition upon an automated analysis of that physical condition, where the score is an indicator of pain felt by the subject.

Voice classifier: This term is used herein to refer to a module of the system that analyzes the inarticulate sounds of the subject.

Voice score: This term is used herein to refer to a value given to the subject's inarticulate sounds upon an automated analysis of those sounds, where the score is an indicator of pain felt by the subject.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall he interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A system for measuring or evaluating pain intensity experienced by a subject, the system comprising:
    an audio/video (A/V) recorder for recording video of facial expressions and body movements of a subject and for recording audio of sounds made by the subject;
    a vital signs reader record vital signs of said subject;
    a facial expression classifier for evaluating pain intensity experienced by the subject from the facial expressions of said subject recorded by the audio/video recorder, said facial expression classifier producing a facial expression score based on said facial expressions of said subject;
    a body movement classifier for evaluating said body movements of said subject recorded by said A/V recorder, said body movement classifier producing a body movement score based on said body movements of said subject;
    a voice classifier for evaluating said pain intensity from the sounds made by said subject recorded by the audio/video recorder, said voice classifier producing a voice score based on said sounds made by said subject;
    a vital signs classifier for evaluating said pain intensity from said vital signs of said subject recorded by said vital signs reader, said vital signs classifier producing a vital signs score based on said vital signs of said subject;
    a processor running that a machine learning algorithm for processing the facial expression score, the body movement score, the voice score and the vital signs score of the subject, and for combining said facial expression score, said body movement score said voice score, and said vital signs score to produce a total score for pain assessment of said subject; and
    an output device for outputting said total score for pain assessment.

2. The system as in claim 1, wherein said A/V recorder comprises a video camera, and a microphone.

3. The system as in claim 1, wherein said motions of said subject indicate one or more of a behavior state, an arousal state and an extremities tone.

4. The system as in claim 1, wherein said vital signs includes a heart rate of said subject.

5. The system as in claim 1, wherein a therapy or intervention is indicated by said output device as a result of said total score exceeding a predetermined pain threshold.

6. The system as in claim 1, wherein said subject is an infant.

7. The system as in claim 1, wherein said facial expression classifier evaluates said pain intensity based on facial strain of said subject.

8. The system as in claim 7, further comprising:
    generating said facial strain for a plurality of facial expressions of said subject; and
    training k Nearest-Neighbor (KNN) and support vector machine (SVM) to classify facial expressions of said subject as pain or no-pain.

9. The system as in claim 7, wherein detection of said facial strain is accomplished via a modified strain algorithm predicated on movement of the face of said subject.

10. The system as in claim 1, further comprising:
    said facial expression classifier segmenting the subject's face into regions in order to provide said facial expression score, and where one or more regions are obstructed or occluded.

11. The system as in claim 1, further comprising:
    said facial expression classifier for performing facial detection where the face of said subject is detected, for performing expression segmentation where said detected subject's face is segmented into regions, and for performing expression recognition of the segmented regions to detect pain of the subject.

12. The system as in claim 11, wherein performing said facial detection further comprises, detecting landmarks on said subject's face to detect said subject's face.

13. The system as in claim 12, wherein said landmarks includes a nose on said subject's face, and wherein a digital mask is expanded around said nose to include eyes and a surrounding area of said subject's face.

14. The system as in claim 12, further comprising:
    training said facial expression classifier using positive images including said landmarks and negative images not including said landmarks.

15. The system as in claim 14, further comprising:
    training said facial expression classifier using an adaptive boosting algorithm.

16. The system as in claim 11, wherein performing expression recognition includes:

generating an optical flow vector for each region of said subject's face, wherein said optical flow vector is used to estimate optical strain for each region;

summing the estimated optical strains for said each region to generate an overall strain magnitude, wherein said overall strain magnitude is related to said facial expressions that can indicate pain experienced by said subject.

17. The system as in claim 11, wherein performing expression recognition includes:

applying a peak detector to detect points of maximum strain, wherein said maximum strain is related to said facial expressions that can indicate pain experienced by said subject.

18. The system as in claim 1, wherein said subject is an infant, and wherein said sounds are crying by said infant.

19. The system as in claim 18, wherein speech signal analysis is used to recognize emotions expressed in said crying by said infant.

20. The system as in claim 1, wherein frequency-based features are extracted from said sounds to represent audio segments that are used to train said voice classifier.

21. The system as in claim 1, further comprising:

said vital signs of said subject further include breathing rate and oxygen saturation in blood of said subject.

22. The system as in claim 1, wherein said machine learning algorithm is parametric or non-parametric.

23. The system as in claim 22, wherein said machine learning algorithm is selected from one or more of the group consisting of facial strain, local binary patterns, linear predictive coding, linear regression, neural network.

24. A method for measuring or evaluating pain intensity experienced by a subject, the method comprising:

recording, with an audio/video (A/V) recorder, facial expressions, sounds, and body movements of a subject, wherein said A/V recorder comprises a video camera for recording video of the facial expressions and body movements and a microphone for recording sounds of the subject;

recording, with a vital signs reader, vital signs of said subject;

evaluating, with a facial expression classifier, pain intensity experienced by the subject from the facial expressions of said subject recorded by the audio/video recorder, said facial expression classifier producing a facial expression score based on said facial expressions of said subject;

evaluating, with a voice classifier, said pain intensity from sounds made by said subject recorded by the audio/video recorder, said voice classifier producing a voice score based on said sounds made by said subject;

evaluating, with a vital signs classifier, said pain intensity, said vital signs classifier producing a vital signs score based on said vital signs recorded by said vital signs reader;

evaluating, with a body movement classifier, said pain intensity from body movements of said subject recorded by said A/V recorder, said body movement classifier producing a body movement score based on said body movements of said subject;

processing, by a processor running a machine learning algorithm, the facial expression score, the voice score and the vital signs score of the subject and combining the facial expression score, the voice score, the vital signs score and the body movement score to produce a total score for pain assessment of said subject.

* * * * *